United States Patent [19]
Nag et al.

[11] Patent Number: 5,734,023
[45] Date of Patent: Mar. 31, 1998

[54] MHC CLASS II β CHAIN/PEPTIDE COMPLEXES USEFUL IN AMELIORATING DELETERIOUS IMMUNE RESPONSES

[75] Inventors: Bishwajit Nag, Pacifica; Brian R. Clark, Redwood City; Somesh Sharma, Los Altos; Harden McConnell, Stanford, all of Calif.

[73] Assignee: Anergen Inc., Redwood City, Calif.

[21] Appl. No.: 483,021

[22] Filed: Jun. 7, 1995

Related U.S. Application Data

[62] Division of Ser. No. 397,533, Mar. 2, 1995, abandoned, which is a continuation of Ser. No. 208,072, Mar. 3, 1994, abandoned, which is a continuation of Ser. No. 978,946, Nov. 18, 1992, abandoned, which is a continuation-in-part of Ser. No. 793,938, Nov. 19, 1991, abandoned.

[51] Int. Cl.$^6$ .................. C07K 14/74; C07K 17/00; A61K 39/385
[52] U.S. Cl. .................. 530/403; 424/185.1; 424/193.1; 530/300; 530/395; 530/402; 530/868
[58] Field of Search .................. 530/300, 350, 530/395, 403, 868, 402; 424/184.1, 185.1, 193.1, 195.1

[56] References Cited

U.S. PATENT DOCUMENTS

| | | | |
|---|---|---|---|
| 4,400,376 | 8/1983 | Sanderson | 424/88 |
| 4,478,823 | 10/1984 | Sanderson | 424/88 |
| 5,130,297 | 7/1992 | Sharma et al. | 514/8 |
| 5,194,425 | 3/1993 | Sharma et al. | 514/8 |

OTHER PUBLICATIONS

Rothenhausler, B., et al., "Specific binding of antigenic molecules of the major histocompatiblity complex" *Proc. Natl. Acad. Sci. USA*, 87:352–354 (1990).

Harding, Clifford V. and Unaune, Emil R., "Quantitation of antigen–presenting cell MHC class II/peptide complexes necessary for T–cell stimulation", *Nature*, 346:574–576 (1990).

Brown, J.H., et al., "Three–dimensional structure of the human class II histocompatibility antigen HLA–DR1", *Nature*, 364:33–39 (1993).

Newsome–Davis, et al., "T–Cell Reactivity in Myasthenia Gravis" *Journal of Autoimmunity*, 2:101–108 (1989).

Hansen, et al., "The Major Histocompatibility Complex" *Fundamental Immunology*, 3d Ed., W. Paul, pp. 617–620 (1993).

Grey, H.M. et al., "How T Cells See Antigen", *Scientific American*, 56–64 (1989).

Buus, S. et al., "Autologous Peptides Constitutively Occupy the Antigen Binding Site on Ia", *Science*, 242:1045–1047 (1988).

Demotz et al., "Characterization of a naturally processed MHC class II–restricted T–cell determinant of hen egg lysozyme", *Nature*, 342:682–684 (1989).

Sinha et al., "Autoimmune Disease: The Failure of Self Tolerance", *Science*, 248:1380–1387 (1990).

Shizuru, J.A. et al., "Immunotherapy of the Nonobese Diabetic Mouse: Treatment with an Antibody to T–Helper LlLymphocytes", *Science*, 240:659–662 (1988).

Schwartz, "Acquisition of Immunologic Self–Tolerance", *Cell*, 1073–1081 (1989).

Quill et al., "Stimulation of Normal Inducer T Cell Clones With Antigen Presented By Purified Ia Molecules in Planar Lipid membranes: Specific Induction of a Long–Lived State of Proliferative Nonresponsiveness", *J. Immunol.*, 138:3704–3712 (1987).

O'Hehir, et al., "The Specificity and Regulation of T–Cell Responsiveness to Allergens", *Ann. Rev. Immunol.*, 9:67–95 (1991).

Passmore, David et al., "Preparative–scale purification and characterization of MHC class II monomers", *J. Immunol.*, 155:193–200 (1992).

Buus, S. et al., "The relation between Major Histocompatibility Complex (MHC) restriction and the Capacity of Ia to bind immunogenic peptides" *Science*, 235:1353–1358 (1987).

Bjorkman, et al., "Structure of the human class I histocompatibility antigen, HLA–A2", *Nature*, 329:512–518 (1987).

Bjorkman, P.J. et al., "The foreign antigen binding site and T cell recognition regions of class I histocompatibility antigens" *Nature*, 329:512–518 (1987).

Marguiles, D.H. et al, "Engineering soluble major histocompatibility molecules: Why and how", *Immunological Research*, 6:101–116 (1987).

Marx, J.L., "Structure of MHC protein solved", *Science*, 329:613–614 (1987).

Townsend, A. et al., "Those images that yet fresh images beget" *Nature*, 329:482–483 (1987).

Nag, Bishwajit et al., Stimulation of T Cells by antigenic peptide complexed with complex class II molecules, *Proc. Natl. Acad. Sci. USA, Immunology*, 90:1604–1608 (1993).

Luescher, I.F., et al., "The Sites in the I–A$^k$ Histocompatibility Molecule Photoaffinity Labeled by an Immunogenic Lysozyme Peptide," *The American Society of Biochemistry and Molecular Biology, Inc.*, vol. 265, No. 19, pp. 11177–11184.

(List continued on next page.)

*Primary Examiner*—Thomas M. Cunningham
*Attorney, Agent, or Firm*—Townsend and Townsend and Crew LLP

[57] ABSTRACT

The present invention is directed to complexes comprising an isolated MHC subunit component, an antigenic peptide and, in some cases, an effector component. The antigenic peptide is associated with the antigen binding site of the MHC subunit component. These complexes are useful in treating autoimmune disease.

7 Claims, 14 Drawing Sheets

OTHER PUBLICATIONS

Wraith, D.C., et al., "Antigen Recognition in Autoimmune Encephalomyelitis and the Potential for Peptide–Mediated Immunotherapy," *Cell*, vol. 59, pp. 247–255 (Oct. 20, 1989).

McCluskey, J., et al. "Cell Surface Expression of an In Vitro Recombinant Class II/Class I Major Histocompatibility Complex Gene Product" *Cell*, 40:247–257 (1985).

Martin, R., et al. "A Myelin Basic Protein Peptide is Recognized by Cytotoxic T Cells in the Context of Four HLA–DR Types Associated with Multiple Sclerosis" *The Journal of Experimental Medicine*, 173:19–24 (1991).

Ota, K., et al., "T–cell recognition of an immunodominant myelin basic protein epitope in multiple sclerosis", *Nature*, 346:183–1187 (1990).

Weaver, Casey T. and Unanue, Emil R., "The costimulatory function of antigen–presenting cells," *Immunology Today*, 11:49–55 (1990).

Golding, H., et al., "T–cell recognition of a chimaeric class II/class I MHC molecule and the role of L3T4", *Nature*, 317:425–427 (1985).

Parce, J., et al., "Detection of Cell–Affecting Agents with a Silicon Biosensor", *Science*, 246:243–247 (1989).

Owicki, J.C., et al., "Continuous Monitoring of receptor––mediated changes in the metabolic rates of living cells" *Proc. Natl. Acad. Sci. USA*, 87:4007–4001 (1990).

Dornmair, K., et al., "In vitro peptide binding to the heavy chain of the class I molecule of the major histocompatibility complex molecule HLA–A2" *Proc. Natl. Acad. Sci. USA*, 88:1335–1338 (1991).

Sharma, S.D. et al., "Antigen–specific therapy experimental allergic encephalomyelitis by soluble class II major histocompatibility complex–peptide complexes", *Proc. Natl. Acad. Sci. USA, Immunology*, 88:11465–11469 (1991).

Nag, Bishwajit et al., "Functionally Active Recombinant $\alpha$ and $\beta$ Chain–Peptide Complexes of Human Major Histocompatibility Class II Molecules", *Journal of Biological Chemistry*, 271:10413–10418 (1996).

Arimilli, Subhashini et al. "Refolding and Reconstitution of Functionally Active Complexes of Human Leukocyte Antigen DR2 and Myelin Basic Protein Peptide from Recombinant $\alpha$ and $\beta$ Polypeptide Chains", *Journal of Biological Chemistry*, 270:971–977, (1995).

Bishwajit, Nag et al., "Intramolecular Charge Heterogeneity in Purified Major Histocompatibility Class II $\alpha$ and $\beta$ Polypeptide Chains", *Journal of Biological Chemistry*, 269:10061–10070, (1994).

Topham, David J. et al., "A synthetic peptide from the third hypervariable region of major histocompatibility complex class II $\beta$ chain as a vaccine for treatment of experimental autoimmune encephalomyelitis", *Proc. Natl. Acad. Sci. USA*, 91:8005–8009, (1994).

Hodes, Richard J. and Terry, William D., "Comparison of irradiated and mitomycin–treated mouse spleen cells as stimulating cells in mixed lymphocyte cultures and in vitro sensitization", *Journal of Immunology*, vol. 113 (1974).

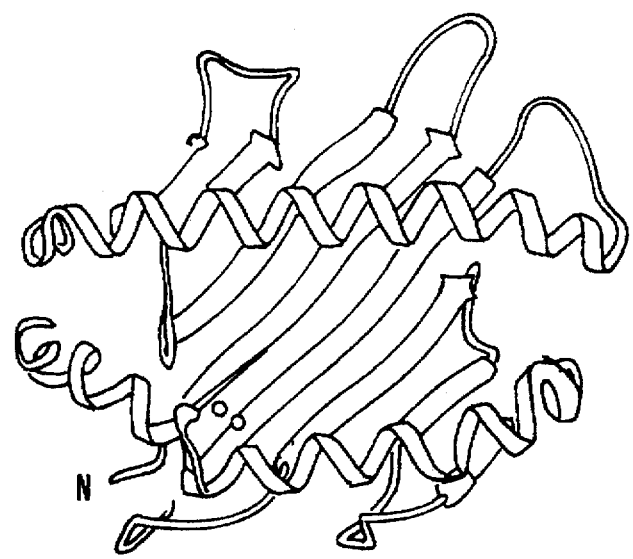
FIG. 1B.
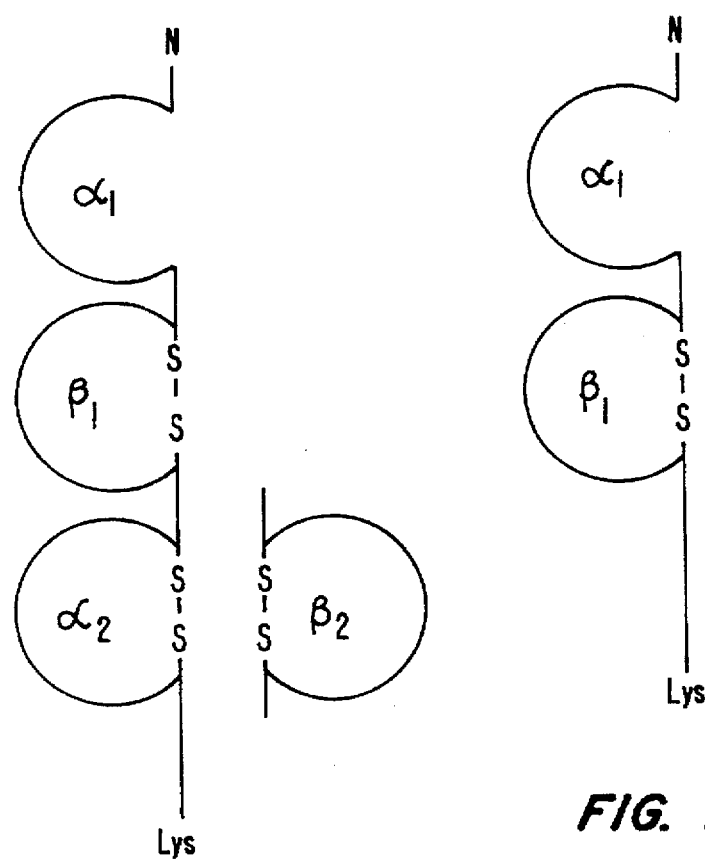
FIG. 2B.
FIG. 2A.

| HPTYP # | FREQ %[2] | DQ | DQBI | DQA1[3] | DRB1 | DRB3 | DRB4 | D | DISEASE ASSOCIATION[4] |
|---|---|---|---|---|---|---|---|---|---|
| 1. | 20 | w5(w1) | 1.1 | 1a | 1 | ne | ne | w1 | IDDM(MAJOR), RA(MINOR) |
| 2. |  | w5(w1) | 1.1 | 1a | 1 | ne | ne | w20 |  |
| 3. | 26 | w6(w1) | 1.2 | 1b | w15(2) | ne | ne | w2 | CPMS, MG (T+) |
| 4. | 1.5 | w6(w1) | 1.12 | 1c | w15(2) | ne | ne | w12 | IDDM(-) |
| 5. | 1.5 | w5(w1) | 1.1 | ? | w16(2) | ne | ne | w21(AZH) | IDDM(+), MG(T-) |
| 6. | ? | w7(w3) | 3.1 | ? | w16(2) | ne | ne | w22 |  |
| 7. | 22 | w2 | ? | ? | w17(3) | 24(52) | ne | w3 |  |
| 8. |  | w2 | ? | ? | w17(3) | 25(52) | ne | w3 | IDDM(+), MG(T-) |
| 9. | ? | w4(Wa) | Wa | ? | w18(3) | ?(52) | ne | ? |  |
| 10. | 9 | w8(w3) | 3.2 | 3 | 4 | ne | 53 | w4(4.2) | IDDM*(+)(MAJOR), RA†(MAJOR), CPMS |
| 11. | 5 | w7(w3) | 3.1 | 3 | 4 | ne | 53 | w4(4.1) |  |
| 12. | 3 | w8(w3) | 3.2 | 3 | 4 | ne | 53 | w10 | IDDM*(+)(MAJOR), CPMS |
| 13. | ? | w7(w3) | 3.1 | 3 | 4 | ne | 53 | w13 |  |
| 14. | 14 | w8(w3) | 3.2 | 3 | 4 | ne | 53 | w14 | IDDM*(+)(MAJOR), RA†(MAJOR), CPMS |
| 15. | 0.5 | w4(Wa) | Wa | ? | 4 | ne | 53 | w15 |  |

FIG. 3A.

| | | | | | | | |
|---|---|---|---|---|---|---|---|
| 16. | 15 | {w7(w3) | 2 | w11(5) | 25(52) | ne | w5 | |
| 17. | | {w7(w3) | 2 | w12(5) | 25(52) | ne | B6 | |
| 18. | 10 | {w5(w1) | 1c | w(13)(w6) | 24(52) | ne | w18 | |
| 19. | | {w5(w1) | 1c | w(13)(w6) | 25(52) | ne | w18 | |
| 20. | 3 | w5(w1) | 1b | w(13)(w6) | 26(52) | ne | w19 | IDDM (MINOR) |
| 21. | 3 | w6(w1) | 1a | w(14)(w6) | 25(52) | ne | w9 | |
| 22. | ? | w6(w1) | 2 | w(14)(w6) | 24(52) | ne | w16 | RA (MINOR) |
| 23. | 1 | w9(w3) | 3 | 7 | ne | 53 | w1 | |
| 24. | 27 | w2 | 3 | 7 | ne | 53 | w17 | |
| 25. | 6 | w4(Wa) | 1b | ne | w8/52 | ne | w8 | |
| 26. | 2 | ?(w3) | 1b | ne | w8/52 | ne | w8 | |
| 27. | 1 | w9(w3) | 3 | 9 | ne | 53 | w23 | |
| 28. | ? | w5(w1) | 1a | w10 | ? | ? | ? | | ne: NOT EXPRESSED
T-: THYMOMA-NEGATIVE
T+: THYMOMA-POSITIVE

CPMS: CHROME-PROGRESSIVE MULTIPLE SCLEROSIS
IDDM: INSULIN-DEPENDENT DIABETES MELLITUS
MG: MYASTHENIA GRAVIS
RA: RHEUMATOID ARTHRITIS

FIG. 3B.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..21
        ( D ) OTHER INFORMATION: /note= "acetylcholine receptor peptide 195- 215"

( x i ) SEQUENCE DESCRIPTION: SEQ ID NO:1:

```
Asp Thr Pro Tyr Leu Asp Ile Thr Tyr His Phe Ile Met Gln Arg Ile
1               5                   10                  15

Pro Leu Tyr Phe Val
            20
```

( 2 ) INFORMATION FOR SEQ ID NO:2:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: -
        ( B ) LOCATION: 1..63
        ( D ) OTHER INFORMATION: /note= "oligonucleotide encoding acetylcholine receptor peptide 195-215"

( x i ) SEQUENCE DESCRIPTION: SEQ ID NO:2:

```
GACACCCGT ACCTGGACAT CACCTACCAC TTCATCATGC AGCGTATCCC GCTGTACTTC      60

CTG                                                                   63
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="Xaa = N-acetyl alanine"

( i x ) FEATURE:
    ( A ) NAME/KEY: Peptide
    ( B ) LOCATION: 1..14
    ( D ) OTHER INFORMATION: /note= "rat myelin basic protein
    peptide analog of MBP(1-14)4-A"

( x i ) SEQUENCE DESCRIPTION: SEQ ID NO:3:

Xaa Ser Gln Ala Arg Pro Ser Gln Arg His Gly Ser Lys Tyr
1               5                   10

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..13
        ( D ) OTHER INFORMATION: /note= "myelin basic protein
        peptide analog MBP(89-101)89-Y"

( x i ) SEQUENCE DESCRIPTION: SEQ ID NO:4:

Tyr Phe Lys Asn Ile Val Thr Pro Arg Thr Pro Pro Pro
1               5                   10

( 2 ) INFORMATION FOR SEQ ID NO:5:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Peptide
        ( B ) LOCATION: 1..18
        ( D ) OTHER INFORMATION: /note= "ovalbumin peptide analog
        OVA(323- 340)340-Y"

( x i ) SEQUENCE DESCRIPTION: SEQ ID NO:5:

Ile Ser Gln Ala Val His Ala Ala His Ala Glu Ile Asn Glu Ala Gly
1               5                   10                  15

Arg Tyr

MHC CLASS II β CHAIN/PEPTIDE COMPLEXES USEFUL IN AMELIORATING DELETERIOUS IMMUNE RESPONSES

CROSS-REFERENCE TO RELATED APPLICATIONS

This is a division of U.S. application Ser. No. 08/397,533, filed Mar. 2, 1995, now abandoned, which is a FWC continuation of U.S. application Ser. No. 08/208,072, filed Mar. 3, 1994, now abandoned, which is a FWC continuation of U.S. application Ser. No. 07/978,946, filed Nov. 18, 1992, now abandoned, which is a continuation-in-part of U.S. application Ser. No. 07/793,938, filed Nov. 19, 1991, now abandoned.

It is related to the following abandoned U.S. patent applications: Ser. No. 07/690,840 (filed Apr. 23, 1991), now U.S. Pat. No. 5,260,422; Ser. No. 07/635,840 (filed Dec. 12, 1990), now U.S. Pat. No. 5,284,935; Ser. No. 07/367,751 (filed Jun. 21, 1989), now U.S. Pat. No. 5,194,125; and Ser. No. 07/210,594 (filed Jun. 23, 1988), now abandoned, all of which are, in their entirety, incorporated herein by reference.

BACKGROUND OF THE INVENTION

The invention relates to the treatment of diseases involving deleterious immune responses and to materials and methods useful in therapy and diagnosis of such diseases. In particular, it concerns complexes which selectively bind T cells and which comprise a subunit from the major histocompatibility complex (MHC) glycoproteins complexed with peptide fragments from antigens associated with these diseases. The complexes themselves are therapeutically useful or they can be further conjugated to radioisotopes or other labels for diagnostic purposes, or to toxins or other substances to specifically eliminate targeted cells.

MHC molecules are heterodimeric glycoproteins expressed on cells of higher vertebrates and play a role in immune responses. In humans, MHC molecules are referred to as HLA (human-leukocyte-associated) antigens because they were first identified in leukocytes. In mice, they are designated H-2 antigens.

MHC molecules are divided into two groups, Class I and Class II, which differ structurally and functionally from each other. In general, the major function of MHC molecules is to bind antigenic peptides and display them on the surface of cells. These peptides result from an antigen presenting cell (APC) processing an antigen into peptide fragments, which can be as short as 8 to 20 amino acids.

Class I MHC molecules are expressed on almost all nucleated cells and are recognized by cytotoxic T lymphocytes, which then destroy the antigen-bearing cells. Class II MHC molecules are expressed primarily on cells involved in initiating and sustaining immune responses, such as T lymphocytes, B lymphocytes, macrophages, etc. Class II MHC molecules are recognized by helper T lymphocytes and induce proliferation of helper T lymphocytes and amplification of the immune response to the particular antigenic peptide that is displayed. For a general discussion of the function of MHC molecules, see Grey, H. M., et al., *Scientific American* November, 1989:56–64, which is incorporated herein by reference.

In addition to binding antigenic peptides, MHC molecules can also bind with autologous, or "self" peptides. If T lymphocytes then respond to cells presenting "self" peptides, a condition of autoimmunity results. See, Buus, S., et al., *Science* 242:1045–1047 (1988); Demotz, et al., *Nature* 342:682–684 (1989). (These publications are incorporated herein by reference.) Over 30 autoimmune diseases are presently known, including myasthenia gravis (MG), multiple sclerosis (MS), systemic lupus erythematosis (SLE), rheumatoid arthritis (RA), insulin-dependent diabetes mellitus (IDDM), etc. Characteristic of these diseases is an attack by the immune system on the tissues of the victim. In nondiseased individuals, such attack does not occur because the immune system is tolerant of "self", i.e., it does not recognize "self" tissues as foreign; however, in persons suffering from autoimmune diseases, such tolerance does not occur and tissue components are recognized as foreign. For a general review of autoimmune disease, see, Sinha et al., *Science* 248:1380–1387 (1990), which is incorporated herein by reference.

The involvement of the MHC Class II proteins in autoimmune disease has been shown in a number of in vitro and animal models. For instance, administration of antibodies to either MHC Class II proteins themselves or antibodies to agents that induce expression of the MHC Class II genes interferes with development of the autoimmune condition. The role of helper T cells has also been demonstrated in animal models using monoclonal antibodies against CD4, which is the characteristic helper T cell surface molecule (Shizuru, J. A. et al., *Science* (1988) 240:659–662). In addition, in vitro assays have demonstrated that anergy or proliferative nonresponsiveness can be induced in lymphocytes by MHC Class II molecules in the absence of an incompletely characterized costimulatory signal (see, Schwartz, *Cell* (1989) 1073–1081 and Quill et al., *J. Immunol.* (1987) 138:3704–3712, which are incorporated herein by reference).

A number of other pathological responses involving unwanted immune responses are known. For instance, a number of allergic diseases, have been associated with particular MHC alleles or suspected of having an autoimmune component. For a review of allergic diseases suitable for treatment using the methods of the present invention see, Ohehire, et al. *Ann. Rev. Immunol.* 9:67–95 (1991), which is incorporated herein by reference. Exemplary allergens include, ragweed, cat allergens, and grass pollen.

Other deleterious T cell-mediated responses include the destruction of foreign cells that are purposely introduced into the body as grafts or transplants from allogeneic hosts. This process, known as "allograft rejection," involves the interaction of host T cells with foreign MHC molecules. Quite often, a broad range of MHC alleles are involved in the response of the host to an allograft.

Current treatment for autoimmune disease and other immunopathologies consists primarily of treating the symptoms, but not intervening in the etiology of the disease. Broad spectrum chemotherapeutic agents which have numerous undesirable side effects are typically employed. Compounds capable of selectively suppressing autoimmune responses at the helper T cell level provide a safer, more effective treatment. In addition, such immunosuppressive compounds are useful in the treatment of nonautoimmune diseases, such as graft versus host disease (GVHD) or various allergic responses. For instance, chronic GVHD patients frequently present conditions and symptoms similar to certain autoimmune diseases.

The inadequate treatments presently available illustrate the urgent need to identify new agents that suppress MHC-restricted immune responses, but avoid undesirable side effects, such as nonspecific suppression of an individual's overall immune response.

SUMMARY OF THE INVENTION

The present invention is directed to methods and compositions that can be used to identify and inhibit those aspects of the immune system which are responsible for undesirable immune responses. Compositions of the present invention are purified complexes comprising an effective portion of a single chain subunit of the MHC-encoded antigen-presenting glycoprotein and an antigenic peptide. These two components may be bound covalently or by noncovalent association. A third component, the effector component, can be included as well. The effector component can be a label, in which case the complexes are used, for instance, to diagnose autoimmune diseases. The effector component can also be a toxin, in which case the complexes are used to selectively eliminate the targeted T cell population.

In other aspects, the invention is directed to pharmaceutical compositions wherein the complexes of the invention are active ingredients. The compositions can be used to down-regulate or eliminate parts of the immune system reactive with, for example, a particular self-antigen associated with an autoimmune disease.

BRIEF DESCRIPTION OF THE DRAWINGS

FIGS. 1A and 1B show the 3-dimensional structure of the human HLA-A2 antigen (Class I).

FIGS. 2A and 2B show preferred second generation MHC protein designs.

FIGS. 3A-3B present a list of the DQ/DR haplotypes in humans and their associations with autoimmune diseases.

DESCRIPTION OF PREFERRED EMBODIMENTS

The invention complexes contain at least two components: an antigenic peptide or other antigenic sequence with the relevant effect on the immune system and an effective portion of a subunit of the MHC-encoded glycoprotein involved in antigen presentation. The association between the peptide antigen and the antigen binding sites of the MHC subunit can be by covalent or noncovalent bonding.

In other embodiments the complexes may also contain an effector component which is generally a toxin or a label. The effector portion may be conjugated to either the MHC subunit or to the antigenic peptide. Each of the components of the system is described separately below; followed by description of the methods by which these complexes can be prepared, evaluated and employed.

The MHC-Derived Component

The glycoproteins encoded by the MHC have been extensively studied in both the human and murine systems. In general, they have been classified as Class I glycoproteins, found on the surfaces of all cells and primarily recognized by cytotoxic T cells; and Class II which are found on the surfaces of several cells, including accessory cells such as macrophages, and are involved in presentation of antigens to helper T cells. Many of the histocompatibility proteins have been isolated and characterized. For a general review of MHC glycoprotein structure and function, see *Fundamental Immunology*, 2d Ed., W. E. Paul, ed., Ravens Press N.Y. 1989, which is incorporated herein by reference.

The Class I MHC in humans is located on chromosome 6 and has three loci, HLA-, HLA-B, and HLA-C. The first two loci have a large number of alleles encoding alloantigens. These are found to consist of a 44 Kd heavy chain subunit and a 12 Kd $\beta_2$-microglobulin subunit which is common to all antigenic specificities. Isolation of these detergent-soluble HLA antigens was described by Springer, T. A., et al., *Proc. Natl. Acad. Sci. USA* (1976) 73:2481–2485; Clementson, K. J., et al., in "Membrane Proteins" Azzi, A., ed; Bjorkman, P., Ph.D. Thesis Harvard (1984) all of which are incorporated herein by reference.

Figure 1A:
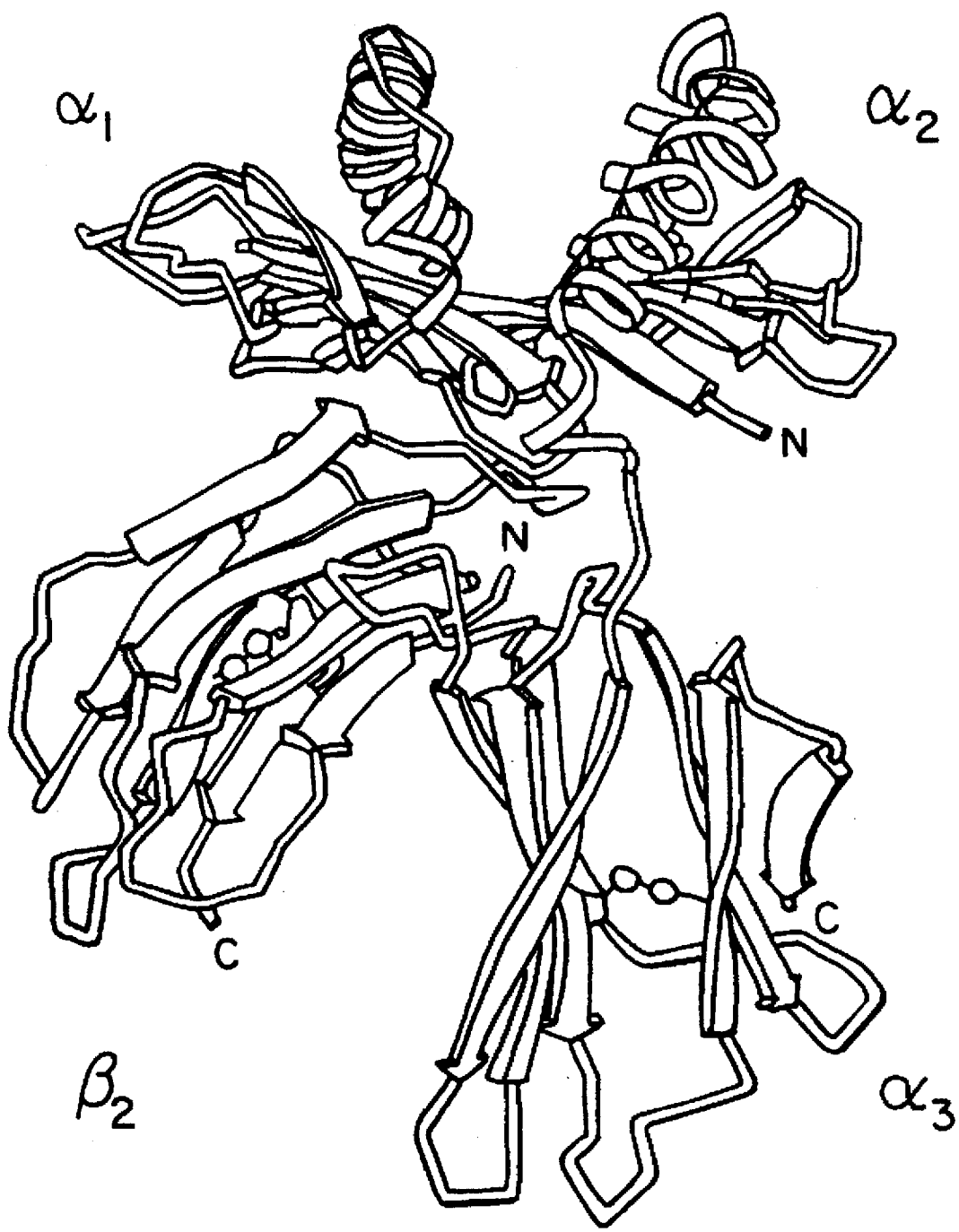

Further work has resulted in a detailed picture of the 3-D structure of HLA-A2, a Class I human antigen. (Bjorkman, P. J., et al., *Nature* (1987) 329:506–518 which is incorporated herein by reference). In FIG. 1 it can be seen that the $\beta_2$-microglobulin protein and $\alpha_3$ segment of the heavy chain are associated. The $\alpha_1$ and $\alpha 2$ regions of the heavy chain form antigen-binding sites to which the peptide is bound (*Science* (1987) 238:613–614, which is incorporated herein by reference) Bjorkman, P. J. et al. *Nature* (supra).

Soluble HLA-A2 can be purified after papain digestion of plasma membranes from the homozygous human lymphoblastoid cell line J-Y as described by Turner, M. J. et al., *J. Biol. Chem.* (1977) 252:7555–7567, which is incorporated herein by reference. Papain cleaves the 44 Kd heavy chain close to the transmembrane region yielding a molecule comprised of $\alpha_1$, $\alpha_2$, $\alpha_3$, and $\beta_2$ microglobulin.

The three dimensional structure of the antigen binding site in Class II MHC antigens is not known in the same detail as that in MHC I. Class II glycoproteins have a general domain structure similar to that of Class I, however. The antigen binding sites of Class II MHC are located on the N-terminal domain portions of the two subunits (the α and β chains). A separate antigen binding site is located on each subunit (see, Luescher et al., J. Biol. Chem. 265:11177–11184 (1990), which is incorporated herein by reference). The two subunits are held together by noncovalent forces and each contains two globular domains ($\alpha_1$, $\alpha_2$ and $\beta_1$, $\beta_2$, respectively) which are all stabilized by disulfide bonds except the $\alpha_1$ domain.

The MHC glycoproteins can be isolated from appropriate cells or can be recombinantly produced. Methods for purifying the murine I-A (Class II) histocompatibility proteins are well known and have been disclosed by Turkewitz, A. P., et al., *Molecular Immunology* (1983) 20:1139–1147, which is incorporated herein by reference. The isolated antigens encoded by the I-A and I-E subregions were shown to consist of two noncovalently bonded peptide chains: an α chain of 32–38 Kd and a β chain of 26–29 Kd. A third, invariant, 31 Kd peptide is noncovalently associated with these two peptides, but it is not polymorphic and does not appear to be a component of the antigens on the cell surface (Sekaly, R. P., *J. Exp. Med.* (1986) 164:1490–1504, which is incorporated herein by reference).

Cloning of the MHC genes (as described by Paul et al, supra, Chapters 16–18) permits ready manipulation of the MHC subunits, as described below. In particular, the α and β chains of seven allelic variants of the I-A region have been cloned and sequenced (Estees, "T cell Clones", pp. 3–19).

The term "isolated MHC subunit component" as used herein refers to an MHC glycoprotein subunit (i.e., an α or β chain of MHC II or a heavy chain of MHC I), which is in other than its native state, for example, not associated with the cell membrane of a cell that normally expresses MHC. This term embraces a full length subunit chain, as well as an effective portion of the MHC subunit. An effective portion is one comprising an antigen binding site and sequences necessary for recognition by the appropriate T cell receptor. It typically comprises at least about 60–80%, typically 90–95% of the sequence of the full-length chain. As described in detail below, the MHC subunit component may be recombinantly produced or solubilized from the appropriate cell source. Although the MHC components are soluble in vivo (i.e., they retain sufficient solubility to function in vivo) they may be associated with detergents to form micelles or with lipids to form liposomes in certain embodiments.

It is well known that native forms of "mature" MHC glycoproteins and subunits will vary somewhat in length because of deletions, substitutions, and insertions or additions of one or more amino acids in the sequences. Thus, MHC subunit components are subject to substantial natural modification, yet are still capable of retaining their respective activities. Modified protein chains can also be readily designed and manufactured utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

In general, modifications of the genes encoding the MHC subunit component may be readily accomplished by a variety of well-known techniques, such as site-directed mutagenesis (see, Gillman and Smith, *Gene* 8:81–97 (1979)

and Roberts, S. et al., *Nature* 328:731–734 (1987), both of which are incorporated herein by reference). One of ordinary skill will appreciate that the effect of many mutations is difficult to predict. Thus, most modifications are evaluated by routine screening in a suitable assay for the desired characteristic. For instance, a change in the immunological character of the subunit can be detected by competitive immunoassay with an appropriate antibody. The effect of a modification on the ability of the subunit to activate T cells can be tested using standard in vitro cellular assays or the methods described in the example section, below. Modifications of other properties such as redox or thermal stability, hydrophobicity, susceptibility to proteolysis, or the tendency to aggregate are all assayed according to standard techniques.

This invention provides amino acid sequence variants of MHC subunits prepared with various objectives in mind, including increasing the affinity of the subunit for antigenic peptides and/or T cell receptors, facilitating the stability, purification and preparation of the subunits. The modified subunits are useful for modifying plasma half life, improving therapeutic efficacy, and lessening the severity or occurrence of side effects during therapeutic use of complexes of the present invention. The amino acid sequence variants of the subunits are usually predetermined variants not found in nature or naturally occurring alleles. The variants typically exhibit the same biological activity (for example, antigenic peptide binding) as the naturally occurring analogue. However, the variants and derivatives that are not capable of binding to their ligands are useful nonetheless (a) as reagents in diagnostic assays for MHC haplotypes or antibodies to the MHC, (b) as agents for purifying anti-MHC antibodies from antisera or hybridoma culture supernatants when insolubilized according to known methods, and (c) as immunogens for raising antibodies to MHC or as immunoassay kit components (labelled, as competitive reagents for the native MHC haplotype or unlabelled as a standard for the MHC assay) so long as at least one MHC epitope remains active.

Insertional variants of the present invention are those in which one or more amino acid residues are introduced into a predetermined site in the MHC subunit and which displace the preexisting residues. For instance, insertional variants can be fusions of heterologous proteins or polypeptides to the amino or carboxyl terminus of the subunits.

Immunogenic fusions are produced by cross-linking in vitro or by recombinant cell culture using DNA encoding an immunogenic polypeptide linked to the appropriate MHC subunit gene. These immunogenic fusions are useful, for instance, to raise antibodies useful in diagnostics or in purification of MHC by immunoaffinity techniques well known to the skilled artisan.

Other fusions, which may or may not also be immunologically active, include fusions of the subunit with a heterologous signal sequence and fusions of the subunit to polypeptides having enhanced plasma half life (ordinarily>about 20 hours) such as immunoglobulin chains or fragments thereof (see, copending application U.S. Ser. No. 07/783,938, which is incorporated hereby reference).

Substitutional variants are those in which at least one residue has been removed and a different residue inserted in its place. Nonnatural amino acid (i.e., amino acids not normally found in native proteins), as well as isosteric analogs (amino acid or otherwise) are also suitable for use in this invention.

Substantial changes in function or immunological identity are made by selecting substituting residues that differ in their effect on maintaining the structure of the polypeptide backbone (e.g., as a sheet or helical conformation), the charge or hydrophobicity of the molecule at the target site, or the bulk of the side chain. The substitutions which in general are expected to produce the greatest changes in function will be those in which (a) a hydrophilic residue, e.g., serine or threonine, is substituted for (or by) a hydrophobic residue, e.g. leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamine or aspartine; or (d) a residue having a bulky side chain, e.g., phenylalanine, is substituted for (or by) one not having a side chain, e.g., glycine.

Substitutional variants of the subunits also include variants where functionally homologous (having at least about 70% homology) domains of other proteins are substituted by routine methods for one or more of the MHC subunit domains. Particularly preferred proteins for this purpose are other members of the immunoglobulin super family.

Another class of variants are deletional variants. Deletions are characterized by the removal of one or more amino acid residues from the MHC subunit sequence. Typically, the transmembrane and cytoplasmic domains are deleted. Deletions of cysteine or other labile residues also may be desirable, for example in increasing the oxidative stability of the MHC complex. Deletion or substitutions of potential proteolysis sites, e.g., ArgArg, is accomplished by deleting one of the basic residues or substituting one by glutaminyl or histidyl residues.

A preferred class of substitutional or deletional variants comprises those involving the transmembrane region of the subunit. Transmembrane regions of MHC subunits are highly hydrophobic or lipophilic domains that are the proper size to span the lipid bilayer of the cellular membrane. They are believed to anchor the MHC molecule in the cell membrane.

Inactivation of the transmembrane domain, typically by deletion or substitution of transmembrane domain hydroxylation residues, will facilitate recovery and formulation by reducing its cellular or membrane lipid affinity and improving its aqueous solubility. Alternatively, the transmembrane and cytoplasmic domains can be deleted to avoid the introduction of potentially immunogenic epitopes. Inactivation of the membrane binding function is accomplished by deletion of sufficient residues to produce a substantially hydrophilic hydropathy profile at this site or by substitution with heterologous residues which accomplish the same result.

A principal advantage of the transmembrane inactivated MHC is that it may be secreted into the culture medium of recombinant hosts. This variant is soluble in body fluids such as blood and does not have an appreciable affinity for cell membrane lipids, thus considerably simplifying its recovery from recombinant cell culture. Typically, subunit variants of this invention will not have a functional transmembrane domain and preferably will not have a functional cytoplasmic sequence. Such variants will consist essentially of the effective portion of the extracellular domain of the MHC subunit. In some circumstances, the subunit comprises sequences from the transmembrane region (up to about 10 amino acids), so long as solubility is not significantly affected.

For example, the transmembrane domain may be substituted by any amino acid sequence, e.g., a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) subunit, these variants are secreted into the culture medium of recombinant hosts.

Glycosylation variants are included within the scope of this invention. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated subunits having the native, unmodified amino acid sequence. For example, substitutional or deletional mutagenesis is employed to eliminate the N- or O-linked glycosylation sites of the subunit, e.g., the asparagine residue is deleted or substituted for by another basic residue such as lysine or histidine. Alternatively, flanking residues making up the glycosylation site are substituted or deleted, even though the asparagine residues remain unchanged, in order to prevent glycosylation by eliminating the glycosylation recognition site. Additionally, unglycosylated subunits which have the amino acid sequence of the native subunits are produced in recombinant prokaryotic cell culture because prokaryotes are incapable of introducing glycosylation into polypeptides.

Glycosylation variants are conveniently produced by selecting appropriate host cells or by in vitro methods. Yeast, for example, introduce glycosylation which varies significantly from that of mammalian systems. Similarly, mammalian cells having a different species (e.g., hamster, murine, insect, porcine, bovine or ovine) or tissue origin (e.g., lung, liver, lymphoid, mesenchymal or epidermal) than the MHC source are routinely screened for the ability to introduce variant glycosylation as characterized for example by elevated levels of mannose or variant ratios of mannose, fucose, sialic acid, and other sugars typically found in mammalian glycoproteins. In vitro processing of the subunit typically is accomplished by enzymatic hydrolysis, e.g., neuraminidase digestion.

MHC glycoproteins suitable for use in the present invention have been isolated from a multiplicity of cells using a variety of techniques including solubilization by treatment with papain, by treatment with 3M KCl, and by treatment with detergent. In a preferred method detergent extraction of Class II protein from lymphocytes followed by affinity purification is used. Detergent can then be removed by dialysis or selective binding beads, e.g., Bio Beads. The molecules can be obtained by isolation from any MHC bearing cell, such as B lymphocytes from an individual suffering from the targeted autoimmune disease. In particular, suitable MHC molecules may be isolated from B cells which have been immortalized by transformation with a replication deficient Epstein-Barr virus, utilizing techniques known in the art.

Isolation of individual subunits from the isolated MHC glycoproteins is easily achieved using standard techniques known to those skilled in the art. For instance, in the case of Class I molecules, the heavy chain can be separated using SDS/PAGE and electroelution of the heavy chain from the gel (see, e.g., Dornmair et al., supra and Hunkapiller, et al., *Methods in Enzymol.* 91:227–236 (1983), which is incorporated herein by reference). Separate α and β subunits from MHC II molecules are also isolated using SDS/PAGE followed by electroelution as described below and in Gorga et al. *J. Biol. Chem.* 262:16087–16094 (1987) and Dornmair et al. *Cold Spring Harbor Symp. Quant. Biol.* 54:409–416

(1989), which are incorporated herein by reference. One of skill will recognize that a number of other standard methods of separating molecules can be used, such as ion exchange chromatography, size exclusion chromatography or affinity chromatography.

Alternatively, the amino acid sequences of a number of Class II proteins are known, and the genes have been cloned, therefore, the subunits can be made using recombinant methods. These techniques allow a number of modifications of the MHC subunits of the present invention. For instance, recombinant techniques provide methods for carboxy terminal truncation which deletes the hydrophobic transmembrane domain. The carboxy termini can also be arbitrarily chosen to facilitate the conjugation of toxins or labels, for example, by introducing cysteine and/or lysine residues into the molecule. The synthetic gene will typically include restriction sites to aid insertion into expression vectors and manipulation of the gene sequence. The genes encoding the appropriate subunits are then inserted into expression vectors, expressed in an appropriate host, such as *E. coli*, yeast, or other suitable cells, and the recombinant proteins are obtained.

As the availability of the gene permits ready manipulation of the sequence, a second generation of preferred construction includes hybrid Class I and Class II features, as illustrated in FIG. 2, wherein the $\alpha_1$ and $\beta_1$ domains of Class II MHC are linked through a flexible portion that permits intramolecular dimerization between these domains resulting in an edge-to-edge $\beta$ sheet contact. The $\beta_1$ segment is then fused to the $\alpha_2$ domain of Class I with $\beta_2$ microglobulin coexpressed to stabilize the complex. The transmembrane and intracellular domains of the Class I gene can also be included but there may be no point in doing so unless liposomes are used to transport the complex. A simpler version includes only the $\alpha_1$ and $\beta_1$ domains with a C-terminal lysine for toxin conjugation (FIG. 2).

Construction of expression vectors and recombinant production from the appropriate DNA sequences are performed by methods known in the art. Standard techniques are used for DNA and RNA isolation, amplification, and cloning. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., 1989, which is incorporated herein by reference. Other general references are provided throughout this document. The procedures therein are believed to be well known in the art and are provided for the convenience of the reader.

Expression can be in procaryotic or eucaryotic systems. Procaryotes most frequently are represented by various strains of *E. coli*. However, other microbial strains may also be used, such as bacilli, for example *Bacillus subtilis,* various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., *Gene* (1977) 2:95. Commonly used procaryotic control sequences, which are defined herein to include promoters for transcription initiation, optionally with an operator, along with ribosome binding site sequences, including such commonly used promoters as the $\beta$-lactamase (penicillinase) and lactose (lac) promoter systems (Change et al., *Nature* (1977) 198:1056) and the tryptophan (trp) promoter system (Goeddel et al., *Nucleic Acids Res.* (1980) 8:4057) and the lambda-derived $P_L$ promoter and N-gene ribosome binding site (Shimatake et al., *Nature* (1981) 292:128). Any available promoter system compatible with procaryotes can be used. All references cited herein whether supra or infra, are hereby incorporated herein by reference.

The expression systems useful in the eucaryotic hosts comprise promoters derived from appropriate eucaryotic genes. A class of promoters useful in yeast, for example, include promoters for synthesis of glycolytic enzymes, including those for 3-phosphoglycerate kinase (Hitzeman, et al., *J. Biol. Chem.* (1980) 255:2073). Other promoters include those from the enolase gene (Holland, M. J., et al. *J. Biol. Chem.* (1981) 256:1385) or the Leu2 gene obtained from YEp13 (Broach, J., et al., *Gene* (1978) 8:121).

Suitable mammalian promoters include the early and late promoters from SV40 (Fiers, et al., *Nature* (1978) 273:113) or other vital promoters such as those derived from polyoma, adenovirus II, bovine papilloma virus or avian sarcoma viruses. Suitable viral and mammalian enhancers are cited above.

The expression system is constructed from the foregoing control elements operably linked to the MHC sequences using standard methods, employing standard ligation and restriction techniques which are well understood in the art. Isolated plasmids, DNA sequences, or synthesized oligonucleotides are cleaved, tailored, and relegated in the form desired.

Site-specific DNA cleavage is performed by treatment with the suitable restriction enzyme (or enzymes) under conditions which are generally understood in the art, and the particulars of which are specified by the manufacturer or these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacrylamide gel or agarose gel electrophoresis using standard techniques. A general description of size separation is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 Mm Tris Ph 7.6, 50 Mm NaCl, 6 mM $MgCl_2$, 6 Mm DTT and 5–10 μM dNTPs. The Klenow fragment fills in a 5' sticky ends but chews back protruding 3' single strands, even through the four dNTPS, are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column.

Synthetic oligonucleotides are prepared using commercially available automated oligonucleotide synthesizers.

Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1–2 mM ATP, 1.7 pmoles $^{32}$P-ATP (2.9 mCi/mmole), 0.1 mM spermidine, 0.1 mM EDTA.

Ligations are performed in 15–30 μl volumes under the following standard conditions and temperatures: 20 mM Tris-HCl pH 7.5, 10 mM MgCl$_2$, 10 mM DTT, 33 ug/ml BSA, 10 mM–50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10 to 30 fold molar excess of linkers) are performed at 1 μM total ends concentration.

In vector construction employing "vector fragments," the vector fragment is commonly treated with bacterial alkaline phosphatase (BAP) in order to remove the 5' phosphate and prevent relegation of the vector. BAP digestions are conducted at pH 8 in approximately 150 mM Tris, in the presence of Na$^+$ and Mg$^{+2}$ using about 1 unit of BAP per μg of vector at 60° C. for about 1 hr. In order to recover the nucleic acid fragments, the preparation is extracted with phenol/chloroform and ethanol precipitated and desalted by application to a Sephadex G-50 spin column. Alternatively, relegation can be prevented in vectors which have been double digested by additional restriction enzyme digestion of the unwanted fragments.

For portions of vectors derived from cDNA or genomic DNA which require sequence modifications, site-specific primer-directed mutagenesis can be used. This is conducted using a primer synthetic oligonucleotide complementary to a single-stranded phage DNA to be mutagenized except for limited mismatching, representing the desired mutation. Briefly, the synthetic oligonucleotide is used as a primer to direct synthesis of a stand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

In the proteins of the invention, however, a synthetic gene is conveniently employed. The gene design can include restriction sites which permit easy manipulation of the gene to replace coding sequence portions with these encoding analogs.

Correct ligations for plasmid construction can be confirmed by first transforming E. coli strain MM294 obtained. from E. coli Genetic Stock Center, CGSC #6135, or other suitable host, with the ligation mixture. Successful transformants are selected by ampicillin, tetracycline or other antibiotic resistance or by using other markers depending on the mode of plasmid construction, as is understood in the art. Plasmid from the transformants are then prepared according to the method of Clewell, D. B., et al., Proc. Natl. Acad. Sci. USA (1969) 62:1159, optionally following chloramphenicol amplification (Clewell, D. B., J. Bacteriol. (1972) 110:667). The isolated DNA is analyzed by restriction and/or sequenced by the dideoxy method of Sanger, F., et al., Proc. Natl. Acad. Sci. USA (1977) 74:5463 as further described by Messing, et al., Nucleic Acids Res. (1981) 9:309, or by the method of Maxam, et al., Methods in Enzymology (1980) 65:499.

The constructed vector is then transformed into a suitable host for production of the protein. Depending on the host cell used, transformation is done using standard techniques appropriate to such cells. The calcium treatment employing calcium chloride, as described by Cohen, S. N., Proc. Natl. Acad. Sci. USA (1972) 69:2110, or the RbCl method described in Maniatis, et al., Molecular Cloning: A Laboratory Manual (1982) Cold Spring Harbor Press, p. 254 is used for procaryotes or other cells which contain substantial cell wall barriers. For mammalian cells without such cell walls, the calcium phosphate precipitation method of Graham and van der Eb, Virology (1978) 52:546 or electroporation is preferred. Transformations into yeast are carried out according to the method of Van Solingen, P., et al., J. Bacter. (1977) 130:946 and Hsiao, C. L., et al., Proc. Natl. Acad. Sci. USA (1979) 76:3829.

The transformed cells are then cultured under conditions favoring expression of the MHC sequence and the recombinantly produced protein recovered from the culture.

Antigenic Peptides

The antigenic proteins or tissues for a number of deleterious immune responses are known. For example, in experimentally induced autoimmune diseases, antigens involved in pathogenesis have been characterized: in arthritis in rat and mouse, native type-II collagen is identified in collagen-induced arthritis, and mycobacterial heat shock protein in adjuvant arthritis (Stuart et al. (1984), Ann. Rev. Immunol. 2:199-218; van Eden et al. (1988), Nature 331:171-173.); thyroglobulin has been identified in experimental allergic thyroiditis (EAT) in mouse (Maron et al. (1988), J. Exp. Med. 152:1115-1120); acetyl choline receptor (AChR) in experimental allergic myasthenia gravis (EAMG) (Lindstrom et al. (1988), Adv. Immunol. 42:233-284); and myelin basic protein (MBP) and proteolipid protein (PLP) in experimental allergic encephalomyelitis (EAE) in mouse and rat (See Acha-Orbea et al., supra). In addition, for example, target antigens have been identified in humans: type-II collagen in human rheumatoid arthritis (Holoshitz et al. (1986), Lancet ii:305-309); and acetyl choline receptor in myasthenia gravis (Lindstrom et al. (1988), supra) all of the above are incorporated herein by reference.

It is believed that the presentation of antigen by the MHC glycoprotein on the surface of antigen-presenting cells (APCs) occurs subsequent to the hydrolysis of antigenic proteins into smaller peptide units. The location of these smaller segments within the antigenic protein can be determined empirically. These segments are thought to be about 8–20 residues in length, and contain both the agretope (recognized by the MHC molecule) and the epitope (recognized by T cell receptor on the T cell). The epitope is a contiguous or noncontiguous sequence of 5–6 amino acids which recognizes the antigen-specific T cell receptor. The agretope is a continuous or noncontiguous sequence which is responsible for the association of the peptide with the MHC glycoproteins.

The empirical process of determining the relevant 8–15 amino acid subunits is illustrated using the α subunit of the acetylcholine receptor of skeletal muscle. In myasthenia gravis (MG) an autoimmune response is directed to a region of this subunit. A loss of the acetylcholine receptors on the postsynaptic membrane of the neuromuscular junction causes the MG symptoms.

In MG, autoantibodies against the α subunit of the acetylcholine receptor (AChR) are associated with the autoimmune response directed at the AChR. Eighty-five percent of MG patients have autoantibodies reactive with the α subunit. Of these, 60% have antibodies that bind to a peptide segment of the α subunit called the main immunogenic region (MIR) which is located between residues 60 and 80 (Tzartos and Lindstrom, *Proc. Natl. Acad. Sci. USA* (1980) 77:755). The peptide segments recognized by autoreactive human T cells also are located on the α subunit (Hohfield, et al., *Proc. Natl. Acad. Sci. USA* (1987). The epitopes recognized by these T cells lie between residues 1–30, 125–147, 169–181, 257–271 and 351–368. In addition, in humans the AChR peptides 195–212 and 257–269 have been partially characterized as epitopes in myasthenia gravis patients of the HLA-DR5 and HLA-DR3, DQw2 MHC haplotypes, respectively (See Acha-Orbea (1989), supra).

The peptides carrying agretopes permitting presentation of the epitopes associated with α subunit of this receptor are readily determined. For example, determination of the appropriate peptides in a mouse model is carried out as follows. Strains of mice which, when immunized with *Torpedo californicus* AChR develop a disease with many of the features of human myasthenia gravis, are used as model. MHC Class II glycoproteins are isolated from spleen cells of mice of this strain using lectin and monoclonal antibody affinity supports. The purified MHC Class II proteins are incorporated into phospholipid vesicles by detergent dialysis. The resultant vesicles are then allowed to fuse to clean glass cover slips to produce on each a planar lipid bilayer containing MHC molecules (Brian and McConnell, *Proc. Natl. Acad. Sci.* USA (1984) 81:6159, which is incorporated herein by reference).

One cover slip containing MHC Class II molecules embedded in the adherent planar lipid membrane is placed in each well of several 24-well culture plates. Each one of the approximately 40 overlapping 20-residue synthetic peptides corresponding to the α subunit sequence and containing one or more radiolabeled amino acid residues (prepared as described below) is placed in a well with cover slip and PBS and allowed to incubate several days. The extent of binding of peptide in the MHC Class II glycoprotein antigen binding site is measured by the amount of radioactivity incorporated into the MHC Class II-planar lipid membrane on the cover slip versus planar lipid membrane alone. Specific incorporation of radioactivity indicates that the bound peptide contains an agretope (MHC Class II peptide binding site) of one of the several species of MHC Class II molecules present in the planar lipid membrane. In this way, the set of agretopes for the α subunit of AChR is defined for the mouse strain that displays the symptoms of MG upon immunization with AChR or purified α subunit.

Next, each of the α subunit synthetic peptide segments that contain an agretope is again incorporated into the antigen binding site of isolated MHC Class II proteins embedded in planar lipid membranes on cover slips. One cover slip is added to each well of a 24-well culture plate, and spleen cells from mice immunized against AChR (and from which strain the adherent MHC Class II proteins were isolated) are added to each well along with irradiated syngeneic antigen presenting cells. T cell activation, as measured by proliferation indicates that the MHC Class II protein-bound peptide contains both an agretope and an epitope for binding to the T cell. Activation of T cells is also determined by measuring lymphokine (IL-2, IL-3) production (see, Quill et al., supra).

The Dupont apparatus and technique for rapid multiple peptides synthesis (RAMPS) is used to synthesize the members of a set of overlapping (10 residue overlap), 20-residue peptides from the α subunit of *Torpedo californicus* AChR. One or more radioactive amino acids is incorporated into each synthetic peptide. The pentafluorphenyl active esters of side chain-protected, FMOC amino acids are used to synthesize the peptides, applying standard stepwise solid-phase peptide synthetic methods, followed by standard side chain deprotection and simultaneous release of the peptide amide from the solid support.

Alternatively the overlapping sequences which include the putative segments of 8–15 amino acids of the antigenic protein, such as acetylcholine receptor protein, can be synthesized by the method of Geysen, H. M., et al. *J. Immun. Meth.* (1987) 102:274, which is incorporated herein by reference. The synthesized radiolabeled peptides are tested by incubating them individually (on the plates) with purified. MHC proteins which have been formulated into lipid membrane bilayers as above.

In multiple sclerosis (MS), which results in the destruction of the myelin sheath in the central nervous system, myelin basic protein (MBP), the major protein component of myelin is the principal autoantigen. Pertinent segments of the MBP protein are also determined empirically, using a strain of mice which develops experimental allergic encephalitis (EAG) when immunized with bovine myelin basic protein.

Systemic lupus erythematosus (SLE) has a complex systemology, but results from an autoimmune response to several tissues including red blood cells. Peptides which are the antigenic effectors of this disease are found, for instance, in the proteins on the surface of red blood cells.

Rheumatoid arthritis (RA) is a chronic inflammatory disease resulting from an immune response to proteins found in the synovial fluid.

Insulin-dependent diabetes mellitus (IDDM) results from autoimmune attack on the β cells within the Islets of Langerhans which are responsible for secretion of insulin. Circulating antibodies to Islets cells surface antigens and to insulin are known to precede IDDM. Critical peptides in eliciting the immune response in IDDM are believed to be portions of the β cell membrane surface proteins.

The relevant antigenic peptide subunits, as they are relatively short, can readily by synthesized using standard automated methods for peptide synthesis. In the alternative, they can be made recombinantly using isolated or synthetic DNA sequences; though this is not the most efficient approach for peptides of this length.

Thus, in summary, a set of labeled test peptides is prepared, and those which bind to MHC in planar lipid membranes containing MHC proteins are shown to contain the agretope.

The identified peptides are then prepared by conventional solid-phase synthesis and the subset which contains epitopes for the disease-inducing helper T cell clones is determined by incubation of the candidate peptides with antigen-presenting cells (APC) (or with isolated MHC complex) and spleen or lymph node T cells immunized with the full-length protein. Successful candidates will stimulate T cell proliferation in this system. This second, smaller, subset represents the suitable peptide component.

The Effector Component

In one embodiment, the complexes of the invention are designed to destroy the immune response to the peptide in question. In this instance, the effector portion of the molecule will be, for example, a toxin, a chemotherapeutic agent, an antibody to a cytotoxic T-cell surface molecule, a lipase, or a radioisotope emitting "hard" e.g., β, radiation. For example, a number of protein toxins are well known in the art including ricin, diphtheria, gelonin, Pseudomonas toxin, and abrin. Chemotherapeutic agents include, for example, doxorubicin, daunorubicin, methotrexate, cytotoxin, and anti-sense RNA. Antibiotics can also be used. In addition, radioisotopes such as yttrium-90, phosphorus-32, lead-212, iodine-131, or palladium-109 can be used. The emitted radiation destroys the target T-cells.

In some cases the toxin or other effector component is entrapped in a delivery system such as a liposome or dextran carrier; in these cases, either the active component or the carrier may be bound in the complex.

The effector component can also be a labelling moeity. Labeled complexes of the present invention can be used in a variety of in vivo or in vitro applications. For any of these purposes, the complexes may be directly labeled. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, etc. Those of ordinary skill in the art will know of other suitable labels for binding to the complexes, or will be able to ascertain such using routine experimentation. The binding of these labels is achieved using standard techniques common to those of ordinary skill in the art.

In vitro uses include, diagnostic applications, T cell typing, isolating or labeling specific cells, and the like. For instance, the complexes of the present invention can be used to assay for potential inhibitors of MHC-T cell interactions. Potential inhibitors can be assayed for the ability to inhibit binding of complexes of the present invention to T cells in the microphysiometer apparatus described above.

For in vivo diagnostic imaging, radioisotopes are typically used in accordance with well known techniques. The radioisotopes may be bound to the protein either directly or indirectly using intermediate functional groups which were well known to those skilled in the art at the time the parent application was filed. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which were well known at the time the parent application was filed. For instance, these and related techniques have been used in the diagnosis of rheumatic diseases (see, Namey, in *Textbook of Rheumatology*, Kelley et al (eds.) Saunders, Philadelphia, 1985, which is incorporated herein by reference). In general, any conventional method for visualizing diagnostic imaging can be used. Usually gamma- and positron-emitting radioisotopes are used for camera imaging and paramagnetic isotopes are used for MRI. Thus, the complexes of the present invention can be used to monitor the course of amelioration of an autoimmune response in an individual. By measuring the increase or decrease in the number of targeted T cells, it is possible to determine whether a particular therapeutic regimen aimed at ameliorating the autoimmune disease is effective.

The effector component can be attached to the MHC subunit or, if its nature is suitable, to the peptide portion. For example, iodine-131 or other radioactive label can often be included in the peptide determinant sequence. Methods for attaching the effector component to the complex are described in detail below.

Formation of the Complex

The elements of the complex can be associated by standard means known in the art. The antigenic peptides can be associated noncovalently with the antigen binding sites of the MHC subunit by, for example, mixing the two components. They can also be covalently bound using standard procedures by, for example, photo affinity labelling, (see e.g., Hall et al., *Biochemistry* 24:5702–5711 (1985), which is incorporated herein by reference). This method has previously been shown to be effective in covalently binding antigen in peptides to antigen-binding pockets. See, e.g., Leuscher et al., *J. Biol. Chem.*, 265:11177–11184 (1990) and Wraith et al., *Cell*, 59:247–255 (1989), which are incorporated herein by reference. Other modes of linkage are obvious to those of skill in the art, and could include, for example, attachment via carbohydrate groups on the glycoproteins, including, e.g., the carbohydrate moieties of the α- and/or β-chains.

Protein effector components can be conjugated to the MHC subunit or peptide by standard dehydration reactions using carbodiimides. Heterobifunctional linkers such as SPDP, glutaraldehyde and the like can also be used.

The sequence of preparing the complex depends on the components in each instance. For example, in a particular protocol, the peptide portion and MHC subunit component are noncovalently associated by contacting the peptide with the MHC subunit component, e.g., by mixing. The effector is then covalently linked, if desired using commercially available linkers, such as SPDP (Pierce Chemicals) to the MHC. Alternatively, the effector and MHC subunit may be first conjugated using a dehydration reaction and the conjugate complexed with the peptide component.

If the effector is itself a protein, the entire complex may be made directly from the appropriate encoding DNA using recombinant methods. For example, the AChR peptide 195–215, which has been characterized as an epitope in MG in humans and in mice, may be connected to the N-terminal antigen binding site of a polypeptide derived from an MHC antigen associated with MG. The amino acid sequence of the AChR peptide (SEQ ID NO:1) in one letter amino acid code is:

DTPYLDITYHFIMQRIPLYFV

An oligonucleotide which encodes the peptide is synthesized using the known codons for the amino acid, preferably those codons which have preferred utilization in the organism which is to be used for expression are utilized in designing the oligonucleotide. Preferred codon utilizations for a variety of organisms and types of cells are known in the art. If, for example, expression is to be in *E. coli*, a suitable oligonucleotide sequence encoding AChR 195–215 could be:

5' GAC ACC CCG TAC CTG GAC ATC ACC TAC CAC TTC ATC ATG CAG CGT ATC CCG CTG TAC TTC CTG 3' (SEQ ID NO:2).

This sequence may then be incorporated (with or without a sequence encoding a peptide loop region) into a sequence encoding the subunit derived from the MHC antigen, utilizing techniques known in the art. The incorporation site will be such that, when the subunit is expressed and folded, the AChR peptide antigen will be available as an epitope for the target T cells.

In one protocol, the AChR 195–215 peptide is attached to the N-terminal end of the appropriate MHC subunit molecule. If the recombinant complex is to be used in mice, for example, the AChR peptide may be incorporated into a sequence encoding either the I-$A^b$-α or I-$A^b$-β chain. If the AChR peptide is to be incorporated into the β chain, for example, the oligonucleotide may be inserted as a replacement for the leader peptide. Methods of replacing sequences within polynucleotides are known in the art, examples of which are described in the section on the construction of plasmids.

A similar protocol may be used for incorporation of the AChR peptide into a sequence encoding a peptide derived from the appropriate human HLA antigen. For example, in humans, the haplotype DR2W2 is associated with MG. Hence, the AChR peptide may be incorporated into, for example, a sequence encoding a β-chain of a DR2 allele. The structural basis in the DR subregion for the major serological specificities DR1–9 are known, as are the sequences encoding the HLA-DR-β chains from a number of DR haplotypes. See, e.g., Bell et al. (1987), *Proc. Natl. Acad. Sci.* USA 84:6234–6238 which are incorporated herein by reference.

Assessment of the Complex

The complexes of the invention can be assayed using an in vitro system or using an in vivo model. In one in vitro system, the complex is incubated with peripheral blood T cells from subjects immunized with, or showing immunity to, the protein or antigen responsible for the condition associated with the peptide of the complex. The successful complexes will selectively bind the syngeneic T cells and prevent proliferation of the T cells even upon stimulation with additional antigen. Alternatively, T cell activation can be measured by detecting IL-2 production or T cell proliferation as measured by 3H-thymidine uptake, or by uptake of 3-(4,5-dimethyl-thiazol-2-7')-2,5 diphenyltetrazolium bromide (MTT).

A preferred method of assessing complexes is the use of a microphysiometer to measure the rate of production of acidic metabolites in T cells. By using this apparatus, interaction of the complexes with T cell receptors can be quickly and easily detected. The physiological basis of the device is the acidity of the principal catabolic products in mammalian cells, lactate and carbon dioxide. The acidity of the cultural medium bathing a small sample of cells can be determined with a light-addressable potentiometric sensor. The rate of acidification is used as a measure of catabolic rate of the cells being assayed. For a discussion of this technique to measure changes in the catabolic rates of target cells, see, Parce et al., *Science* 246:243–247 (1989) and Owicki et al., *Proc. Natl. Acad. Sci.* (USA) 87:4007–4011 (1990), which are incorporated herein by reference.

In the in vivo system, T cells that proliferate in response to the isolated epitope or to the full-length antigen in the presence of APC are cloned. The clones are injected into histocompatible animals which have not been immunized in order to induce the autoimmune disease. Symptoms related to the relevant complex should ameliorate or eliminate the symptoms of the disease.

Either of the types of complexes, i.e., with or without the effector component, may be used. In one mode the treatment is two-fold. The individual is treated with the complex of an MHC subunit containing an effective portion of the antigen to down-regulate the immune system. Further down-regulation is achieved by treatment with the three component complex which includes the MHC subunit, an effective portion of antigen which is specific for the autoimmune disease being treated, and an effector component. In addition, panels of complexes may be used for treatment. For example, if it is suspected that more than one peptide of an antigen is involved in the autoimmune response, and/or if it is suspected that more than one antigen is involved, the individual may be treated with several complexes. The complexes are selected from a panel containing the effective portion of the appropriate MHC subunit, and effective portions of antigens. The complexes may further comprise effector components, if desired.

Selection of the MHC Complexes for Therapy and/or Diagnosis

In order to select the MHC subunit complexes of the invention which are to be used in the diagnosis or treatment of an individual for a disease, the type of MHC antigens which are involved in the presentation of the antigen or allergen are identified.

For instance, specific autoimmune dysfunctions are correlated with specific MHC types. A list of the DQ/DR haplotypes in humans and their associations with autoimmune diseases are shown in FIG. 3. Methods for identifying which alleles, and subsequently which MHC encoded polypeptides, are associated with a disease are known in the art.

A method described in EP 286447 (which is incorporated herein by reference) is suitable. In this method several steps are followed. First, the association between an MHC antigen and the disease is determined based upon genetic studies. The methods for carrying out these studies are known to those skilled in the art, and information on all known HLA disease associations in humans is maintained in the HLA and Disease Registry in Copenhagen. The locus encoding the polypeptide associated with the disease is the one that would bear the strongest association with the disease (See FIG. 3).

Second, specific alleles encoding the disease associated with MHC antigen/polypeptide are identified. In the identification of the alleles, it is assumed that the susceptibility allele is dominant. Identification of the allele is accomplished by determining the strong positive association of a specific subtype with the disease. This may be accomplished in a number of ways, all of which are known to those skilled in the art. E.g., subtyping may be accomplished by mixed lymphocyte response (MLR) typing and by primed lymphocyte testing (PLT). Both methods are described in Weir and Blackwell, eds., *Handbook of Experimental Immunology*, which is incorporated herein by reference. It may also be accomplished by analyzing DNA restriction fragment length polymorphism (RFLP) using DNA probes that are specific for the MHC locus being examined. E.g., Nepom (1986), Annals N.Y. Acad. Sci. 475, 1 (which is incorporated herein by reference). Methods for preparing probes for the MHC loci are known to those skilled in the art. See, e.g., Gregersen et al. (1986), *Proc. Natl. Acad. Sci.* USA 79:5966; Weissman et al. in Medicine in Transition: the Centennial of the University of Illinois College of Medicine (E. P. Cohen, ed. 1981) all of which are incorporated herein by reference.

The most complete identification of subtypes conferring disease susceptibility is accomplished by sequencing of genomic DNA of the locus, or cDNA to mRNA encoded within the locus. The DNA which is sequenced includes the section encoding the hypervariable regions of the MHC encoded polypeptide. Techniques for identifying specifically desired DNA with a probe, for amplification of the desired region are known in the art, and include, for example, the polymerase chain reaction (PCR) technique.

Once the allele which confers susceptibility to the specific autoimmune disease is identified, the polypeptide encoded within the allele is also identifiable, i.e., the polypeptide sequence may be deduced from the sequence of DNA within the allele encoding it. The MHC subunit complexes of the invention used for diagnosis and/or therapy are derived from the effective portion of the MHC subunit associated with the autoimmune disease state and from an autoimmune antigen associated with the same disease state.

The next step is to identify the appropriate antigen. Several autoantigens which are associated with autoimmune diseases have been extensively studied. Identified autoantigens include acetylcholine receptor in myasthenia gravis, myelin basic protein in multiple sclerosis, mitochondrial dihydrolipoamide acyltransferase in primary biliary cirrhosis, type II collagen in rheumatoid arthritis, thyroglobulin in autoimmune thyroiditis, S antigen in autoimmune uveitis, and desmoplakin I in paraneoplastic pemphigus. In most autoimmune diseases, small autoantigenic peptide fragments (epitopes) of the macromolecular autoantigen have been shown to be recognized by a defined subset of helper T cells.

Once a macromolecular antigen has been identified as the target of an immunopathological response, several published techniques are used to identify and characterize the epitope. These methods generally use antigenic fragments generated by enzymatic digestion of the whole autoantigen or by cloning and expression of fragments of the gene encoding the autoantigen. When the amino acid sequence of the antigenic peptide fragment is known, sets of overlapping peptides are then synthesized. These methods identify epitopic sequences by the ability of the fragments or synthetic peptides to stimulate disease associated T cell clones or hybridomas in syngeneic antigen-presenting systems. See, e.g., Livingstone et al. *Ann. Rev. Immunol.* 5:477–501 (1987); Watts et al. *Ann. Rev. Immunol.* 5:461–475 (1987); Lamb et al. *EMBO J.* 6:1245–1249 (1987); Berkower et al. *J. Immunol.* 136:2498 (1986); Townsend et al., *Cell* 44:959–968 (1986), and Ota et al., *Nature*, 346:183–187 (1990), all of which are incorporated herein by reference.

As an example, over 90% of rheumatoid arthritis patients have a haplotype of DR4(Dw4), DR4(Dw14) or DR1 (See FIG. 3). It is also known that a target antigen in human rheumatoid arthritis is type-II collagen. Hence, the complexes of the invention used for treatment or diagnosis of an individual with rheumatoid arthritis would include those containing a polypeptide derived from the DR4(Dw4), DR1 and/or DR4(Dw14) which is capable of antigen presentation for disease induction, or incapable of antigen presentation for disease suppression, complexed with an effective portion of type-II collagen.

Figure 4:
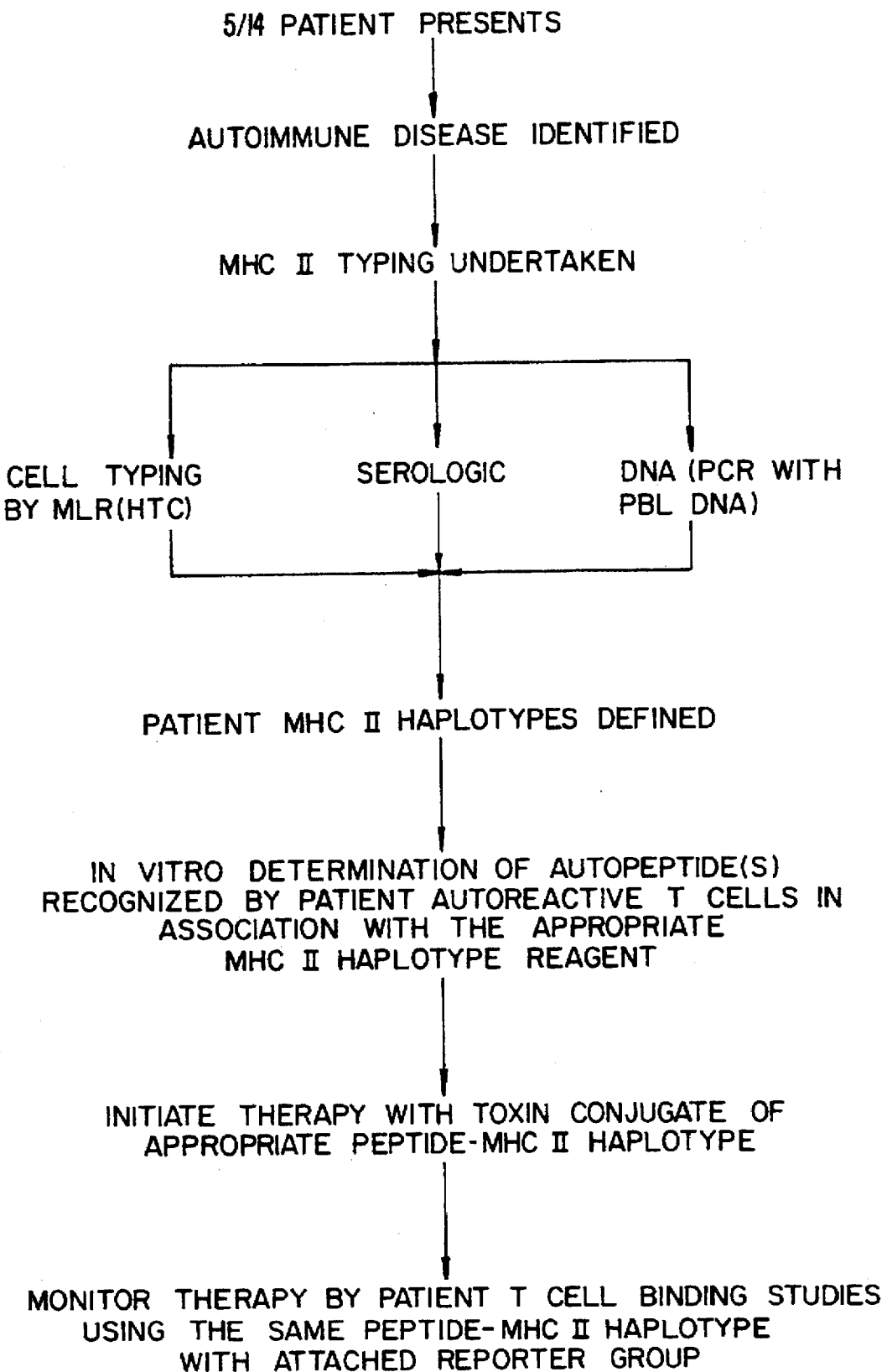
FIG. 4 shows a protocol suitable for the utilization of the complexes of the invention for the diagnosis and/or treatment of an autoimmune disease.
Figure 5A:
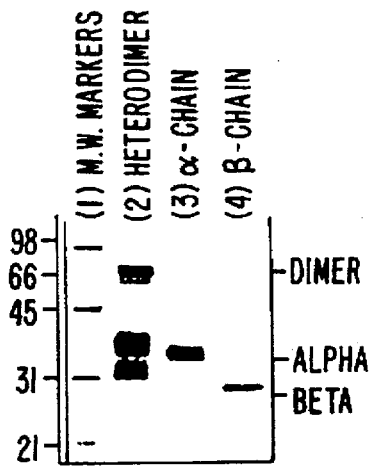
FIG. 5A is an SDS polyacrylamide gel showing separation of $\alpha$ and $\beta$ chains dissociated by heating at 95° for 5 minutes.
Figure 5B:
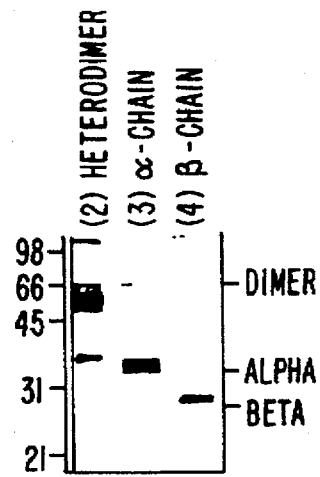
FIG. 5B is an SDS polyacrylamide gel showing separation of $\alpha$ and $\beta$ chains dissociated by low pH.
Figure 5C:
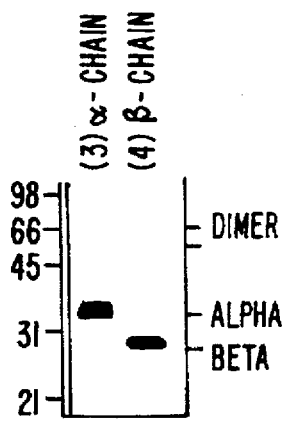
FIG. 5C is SDS-PAGE analysis of single-chain preparations after reduction with 2-ME.
Figure 5D:
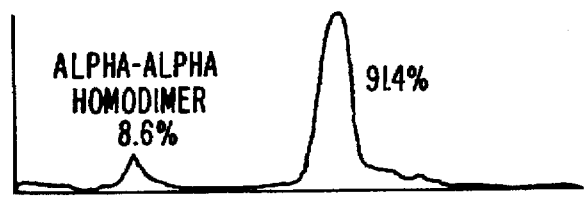
FIG. 5D shows a scan of lane 3 from FIG. 5B
Figure 5E:
FIG. 5E shows a scan of lane 4 from FIG. 5B.
Figure 6A:
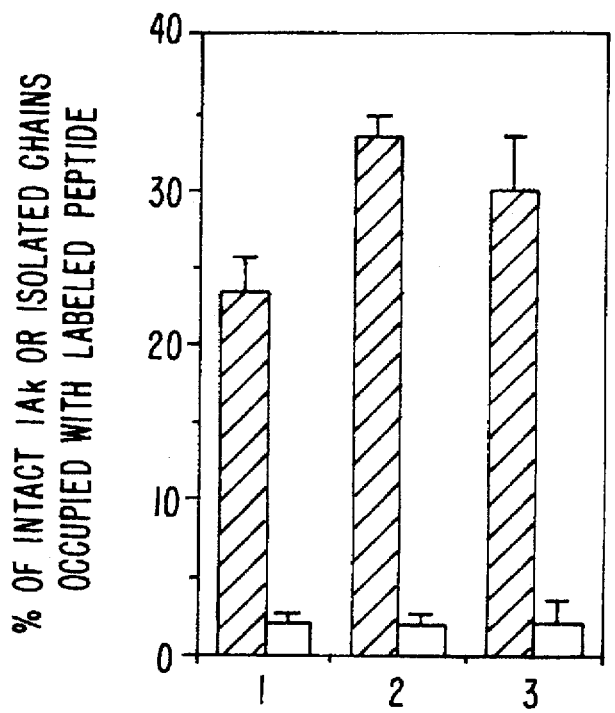
FIG. 6A presents results of peptide binding assays using silica gel TLC.
Figure 6B:
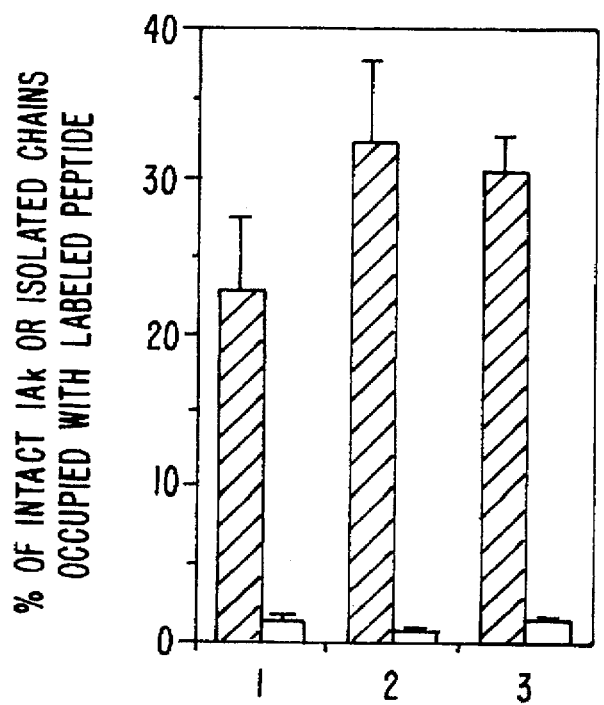
FIG. 6B present results of peptide binding assays using CAE.

A protocol which may be suitable for the utilization of the complexes of the invention for the diagnosis and/or treatment of an autoimmune disease is depicted in FIG. 4. Briefly, an individual having (or susceptible to) an autoimmune disease is identified, and the autoimmune dysfunction is identified. Identification may be by symptomology and/or an examination of family histories. The individual's MHC type is determined by one or more of several methods known in the art, including, for example, cell typing by MLR, by serologic assay, and by DNA analysis (including RFLP and PCR techniques). The individuals T cells are examined in vitro, to determine the autopeptide(s) recognized by autoreactive T cells; this is accomplished utilizing labeled complexes of the invention, described, above. After it is determined which complexes target the T cells, the individual is treated with complexes of the invention which are able to suppress the specific autoreactive T cell replication and/or those which kill the autoreactive T cells. Therapy (as determined by the autoreactive T cells remaining) is monitored with T cell binding studies using the labeled complexes of the invention, described, above.

As used herein, the term "individual" encompasses all mammals and all vertebrates which possess basically equivalent MHC systems.

Model Systems for In vivo Testing

The following are model systems for autoimmune diseases which can be used to evaluate the effects of the complexes of the invention on these conditions.

Systemic Lupus Erythematosus (SLE)

$F_1$ hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans. Knight, et al., *J. Exp. Med.* (1978) 147:1653, which is incorporated hereby by reference.

In both the human and murine forms of the disease, a strong association with MHC gene products has been reported. HLA-DR2 and HLA-DR3 individuals are at a higher risk than the general population to develop SLE (Reinertsen, et al., *N. Engl. J. Med* (1970) 299:515), while in NZB/W $F_1$ mice (H-$2^{d/u}$), a gene linked to the h-$2^u$ haplotype derived from the NZW parent contributes to the development of the lupus-like nephritis.

The effect of the invention complex can be measured by survival rates and by the progress of development of the symptoms, such as proteinuria and appearance of anti-DNA antibodies.

Proteinuria is measured calorimetrically by the use of Uristix (Miles Laboratories, Inc., Elkhart, Ind.), giving an approximation of proteinuria as follows: trace, 10 mg/dl; 1+, 30 mg/dl; 2+, 100 mg/dl; 3+, 300 mg/dl; and 4+, 1000 mg/dl. The development of high grade proteinuria is significantly delayed by treatment of the mice with complex.

The presence of anti-DNA specific antibodies in NZB/W $F_1$ mice is determined by using a modification of a linked immunosorbent assay (ELISA) described by Zouali and Stollar, *J. Immunol. Methods* (1986) 90:105 which is incorporated herein by reference.

Myasthenia Gravis (MG)

Myasthenia gravis is one of several human autoimmune diseases linked to HLA-D. Safenberg, et al., *Tissue Antigens* (1978) 12:136; McDevitt, et al., *Arth. Rheum.* (1977) 20:59 which are incorporated herein by reference. In MG, antibodies to the acetylcholine receptors (AcChoR) impair neuromuscular transmission by mediating loss of AcChoR in the postsynaptic membrane.

SJL/J female mice are a model system for human MG. In these animals, experimental autoimmune myasthenia gravis (EAMG) is induced by immunizing the mice with soluble AcChoR protein from another species. Susceptibility to EAMG is linked in part to the MHC and has been mapped to the region within H-2. Christadoss, et al., *I. Immunol.* (1979) 123:2540.

AcChoR protein is purified from *Torpedo californica* and assayed according to the method of Waldor, et al., *Proc. Natl. Acad. Sci.* (USA) (1983) 80:2713, incorporated by reference. Emulsified AcChoR, 15 µg in complete Freund adjuvant, is injected intradermally among six sites on the back, the hind foot pads, and the base of the tail. Animals are reimmunized with this same regimen 4 weeks later.

Evaluation can be made by measurement of anti-AcChoR antibodies, Anti-AcChoR antibody levels are measured by a microliter ELISA assay as described in Waldor, et al., supra. The standard reagent volume is 50 µl per well. Reagents are usually incubated in the wells for 2 hr at RT. Five µg of AcChoR diluted in bicarbonate buffer, pH 9.6, is added to each well. After incubation with AcChoR, the plates are rinsed four times with a wash solution consisting of phosphate-buffer saline containing 0.05% Tween and 0.05% $NaN_3$. Mouse sera are diluted in 0.01M PBS (pH 7.2), 1.5 mM $MgCl_2$, 2.0 mM 2-mercaptoethanol, 0.05% Tween-80, 0.05% $NaN_3$ (P-Tween buffer) and incubated on the plate. After the plate is washed, β-galactosidase-conjugated sheep anti-mouse antibody diluted in P-Tween buffer is added to each well. After a final washing, the enzyme substrate, p-nitrophenyl-galctopyranoside is added to the plate, and the degree of substrate catalysis is determined from the absorbance at 405 nm after 1 hr.

Anti-AcChoR antibodies are expected to be present in the immunized with AcChoR mice as compared to nonimmunized mice. Treatment with complex is expected to significantly reduce the titer of anti-AcChoR antibodies in the immunized mice.

The effect of treatment with complex on clinical EAMG can also be assessed. Myasthenia symptoms include a characteristic hunched posture with drooping of the head and neck, exaggerated arching of the back, splayed limbs, abnormal walking, and difficulty in righting. Mild symptoms are present after a standard stress test, and should be ameliorated by administration of complex after a period of time after which antibody titer has fallen.

Rheumatoid Arthritis (RA)

In humans, susceptibility to rheumatoid arthritis is associated with HLA D/DR. The immune response in mice to native type II collagen has been used to establish an experimental model for arthritis with a number of histological and pathological features resembling human RA. Susceptibility to collagen-induced arthritis (CIA) in mice has been mapped to the H-2 I region, particularly the I-A subregion. Huse, et al., *Fed. Proc.* (1984) 43:1820.

Mice from a susceptible strain, DBA-1 are caused to have CIA by treatment of the mice with native type II collagen, using the technique described in Wooley and Luthra, *J. Immunol.* (1985) 134:2366, incorporated herein by reference.

In another model, adjuvant arthritis in rats is an experimental model for human arthritis, and a prototype of autoimmune arthritis triggered by bacterial antigens, Holoschitz, et al., *Prospects of Immunology* (CRC Press) (1986); Pearson *Arthritis Rheum.* (1964) 7:80. The disease the result of a cell-mediated immune response, as evidenced by its transmissibility by a clone of T cells which were reactive against the adjuvant (MT); the target self-antigen in the disease, based upon studies with the same cloned cells, appears to be part(s) of a proteoglycan molecule of cartilage.

Adjuvant disease in rats is produced as described by Pearson, supra, i.e., by a single injection of Freund's adjuvant (killed tubercle bacilli or chemical fractions of it, mineral oil, and an emulsifying agent) given into several depot sites, preferably intracutaneously or into a paw or the base of the tail. The adjuvant is given in the absence of other antigens.

The effect of complex treatment of manifestations of the disease are monitored. These manifestations are histopathological, and include an acute and subacute synovitis with proliferation of synovial lining cells, predominantly a mononuclear infiltration of the articular and particular tissues, the invasion of bone and articular cartilage by connective tissue pannus, and periosteal new bone formation, especially adjacent to affected joints. In severe or chronic cases, destructive changes occur, as do fibrous or bony ankylosis. These histopathological symptoms are expected to appear in control animals at about 12 days after sensitization to the Freund's adjuvant.

Insulin Dependent Diabetes Mellitus (IDDM)

IDDM is observed as a consequence of the selective destruction of insulin-secreting cells within the Islets of Langerhans of the pancreas. Involvement of the immune system in this disease is suggested by morphologic evidence of early infiltration of the Islets by mononuclear cells, by the detection of anti-islet cell antibodies, by the high frequency of HLA-DR3 and -DR4 alleles in IDDM populations, and by clinical associations between IDDM and various autoimmune diseases. An animal model for spontaneous IDDM and thyroiditis has been developed in the BB rat. As in humans, the rat disease is controlled in part by the genes encoding the MHC antigens, is characterized by islet infiltration, and is associated with the presence of anti-islet antibodies. The I-E equivalent Class II MHC antigens appear to be involved in manifestation of the autoimmune diseases in the BB rat. Biotard, et al., *Proc. Natl. Acad. Sci.* USA (1985) 82:6627.

In morphologic evaluation, insulitis is characterized by the presence of mononuclear inflammatory cells within the islets. Thyroiditis is characterized by focal interstitial lymphocytic infiltrate within the thyroid gland, as a minimum criterion. Most severe cases show diffuse extensive lymphocytic infiltrates, disruption of acini, fibrosis, and focal Hurthle cell change. See Biotard et al., supra.

Treatment of the BB rats with complex of the invention is expected to ameliorate or prevent the manifestation of the clinical and morphological symptoms associated with IDDM and thyroiditis.

In another spontaneous model, the NOD mouse strain ($H-2K^dD^b$) is a murine model for autoimmune IDDM. The disease in these animals is characterized by anti-islet cell antibodies, severe insulitis, and evidence for autoimmune destruction of the β-cells. Kanazawa, et al., *Diabetologia* (1984) 27:113. The disease can be passively transferred with lymphocytes and prevented by treatment with cyclosporin-A (Ikehara, et al., *Proc. Natl. Acad. Sci.* USA (1985) 82:7743; Mori, et al.), *Diabetologia* (1986) 29:244. Untreated animals develop profound glucose intolerance and ketosis and succumb within weeks of the onset of the disease. Seventy to ninety percent of female and 20–30% of male animals develop diabetes within the first six months of life. Breeding studies have defined at least two genetic loci responsible for disease susceptibility, one of which maps to the MHC. Characterization of NOD Class II antigens at both the serologic and molecular level suggest that the susceptibility to autoimmune disease is linked to I-$A_g$. Acha-Orbea and McDevitt, *Proc. Natl. Acad. Sci. USA* (1970) 84:235.

Treatment of Female NOD mice with complex is expected to lengthen the time before the onset of diabetes and/or to ameliorate or prevent the disease.

Experimental Allergic Encephalomyelitis (EAE)

Experimental allergic encephalomyelitis (EAE) is an induced autoimmune disease of the central nervous system which mimics in many respects the human disease of multiple sclerosis (MS). The disease can be induced in many species, including mice and rats.

The disease is characterized by the acute onset of paralysis. Perivascular infiltration by mononuclear cells in the CNS is observed in both mice and rats. Methods of inducing the disease, as well as symptomology, are reviewed in Aranson (1985) in *The Autoimmune Diseases* (eds. Rose and Mackay, Academic Press, Inc.) pp. 399–427, and in Acha-Orbea et al. (1989), *Ann. Rev. Imm.* 7:377–405.

One of the genes mediating susceptibility is localized in the MHC class II region (Moore et al. (1980), *J. Immunol.* 124:1815–1820). The best analyzed encephalitogenic protein is myelin basic protein (MBP), but other encephalitogenic antigens are found in the brain. The immunogenic epitopes have been mapped (see Acha-Orbea et al., supra.). In the PL mouse strains (H-$2^u$) two encephalitogenic peptides in MBP have been characterized: MBP peptide p35–47 (MBP 35–47), and acetylated (MBP 1–9).

The effect of the invention complexes on ameliorating disease symptoms in individuals in which EAE has been induced can be measured by survival rates, and by the progress of the development of symptoms.

Formulation and Administration

If the transmembrane region of the MHC subunit is included, the complexes of the invention are conveniently administered after being incorporated in lipid monolayers or bilayers. Typically liposomes are used for this purpose but any form of lipid membrane, such as planar lipid membranes or the cell membrane of a cell (e.g., a red blood cell) may be used. The complexes are also conveniently incorporated into micelles. The data presented in Example 2, below, shows that MHC-peptide complexes comprising dimeric MHC molecules exist, primarily as aggregates.

Liposomes can be prepared according to standard methods, as described below. However, if the transmembrane region is deleted, the complex can be administered in a manner conventionally used for peptide-containing pharmaceuticals.

Administration is systemic and is effected by injection, preferably intravenous, thus formulations compatible with the injection route of administration may be used. Suitable formulations are found in *Remington's Pharmaceutical Sciences*, Mack Publishing Company, Philadelphia, Pa., 17th ed. (1985), which is incorporated herein by reference. A variety of pharmaceutical compositions comprising complexes of the present invention and pharmaceutically effective carriers can be prepared. The pharmaceutical compositions are suitable in a variety of drug delivery systems. For a brief review of present methods of drug delivery, see, Langer, *Science* 249:1527–1533 (1990) which is incorporated herein by reference.

In preparing pharmaceutical compositions of the present invention, it is frequently desirable to modify the complexes of the present invention to alter their pharmacokinetics and biodistribution. For a general discussion of pharmacokinetics, see, *Remington's pharmaceutical sciences*, supra, Chapters 37–39. A number of methods for altering pharmacokinetics and biodistribution are known to one of ordinary skill in the art (see, e.g., Langer, supra). For instance, methods suitable for increasing serum half-life of the complexes include treatment to remove carbohydrates which are involved in the elimination of the complexes from the bloodstream. Preferably, substantially all of the carbohydrate moieties are removed by the treatment. Substantially all of the carbohydrate moieties are removed if at least about 75%, preferably about 90%, and most preferably about 99% of the carbohydrate moieties are removed. Conjugation to soluble macromolecules, such as proteins, polysaccharides, or synthetic polymers, such as polyethylene glycol, is also effective. Other methods include protection of the complexes in vesicles composed of substances such as proteins, lipids (for example, liposomes), carbohydrates, or synthetic polymers.

Liposomes of the present invention typically contain the MHC-peptide complexes positioned on the surface of the liposome in such a manner that the complexes are available for interaction with the T cell receptor. The transmembrane region is usually first incorporated into the membrane at the time of forming the membrane. The liposomes can be used to target desired drugs (e.g. toxins or chemotherapeutic agents) to particular autoreactive T cells. Alternatively, the complexes embedded in the liposome may be used to induce anergy in the targeted cells.

Liposome charge is an important determinant in liposome clearance from the blood, with negatively charged liposomes being taken up more rapidly by the reticuloendothelial system (Juliano, *Biochem. Biophys. Res. Commun.* 63:651 (1975)) and thus having shorter half-lives in the bloodstream. Liposomes with prolonged circulation half-lives are typically desirable for therapeutic and diagnostic uses. For instance, liposomes which can be maintained from 8, 12, or up to 24 hours in the bloodstream are particularly preferred.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serve to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, may provide increased circulation of the liposome preparation in the bloodstream, as generally described in U.S. Pat. No. 4,837,028, incorporated herein by reference.

Additionally, the liposome suspension may include lipid-protective agents which protect lipids against free-radical and lipid-peroxidative damages on storage. Lipophilic free-radical quenchers, such as α-tocopherol and water-soluble iron-specific chelators, such as ferrioxianine, are preferred.

A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, all of which are incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powderlike form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration which is desired in the interior volume of the liposomes in the final liposome suspension. Typically the drug solution contains between 10–100 mg/ml of the complexes in a buffered saline solution.

Following liposome preparation, the liposomes may be sized to achieve a desired size range and relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposome to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size.

Even under the most efficient encapsulation methods, the initial sized liposome suspension may contain up to 50% or more complex in a free (nonencapsulated) form.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a replacement medium. Alternatively, gel filtration can be used to separate large liposome particles from solute molecules.

Following the above treatment, the liposome suspension is brought to a desired concentration for use in intravenous administration. This may involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposomes comprising the MHC-peptide complex may be administered parenterally or locally in a dose which varies according to, e.g., the manner of administration, the drug being delivered, the particular disease being treated, etc.

Micelles are commonly used in the art to increase solubility of molecules having nonpolar regions. One of skill will thus recognize that micelles are useful in compositions of the present invention. Micelles comprising the complexes of the invention are prepared according to methods well known in the art (see, e.g., Remington's *Pharmaceutical sciences*, supra, Chap. 20). Micelles comprising the complexes of the present invention are typically prepared using standard surfactants or detergents.

Micelles are formed by surfactants (molecules that contain a hydrophobic portion and one or more ionic or otherwise strongly hydrophilic groups) in aqueous solution. As the concentration of a solid surfactant increases, its monolayers adsorbed at the air/water or glass/water interfaces become so tightly packed that further occupancy requires excessive compression of the surfactant molecules already in the two monolayers. Further increments in the amount of dissolved surfactant beyond that concentration cause amounts equivalent to the new molecules to aggregate into micelles. This process begins at a characteristic concentration called "critical micelle concentration".

The shape of micelles formed in dilute surfactant solutions is approximately spherical. The polar head groups of the surfactant molecules are arranged in an outer spherical shell whereas their hydrocarbon chains are oriented toward the center, forming a spherical core for the micelle. The hydrocarbon chains are randomly coiled and entangled and the micellar interior has a nonpolar, liquid-like character. In the micelles of polyoxyethylated nonionic detergents, the polyoxyethlene moieties are oriented outward and permeated by water. This arrangement is energetically favorable since the hydrophilic head groups are in contact with water and the hydrocarbon moieties are removed from the aqueous medium and partly shielded from contact with water by the polar head groups. The hydrocarbon tails of the surfactant molecules, located in the interior of the micelle, interact with one another by weak van der Waals forces.

The size of a micelle or its aggregation number is governed largely by geometric factors. The radius of the hydrocarbon core cannot exceed the length of the extended hydrocarbon chain of the surfactant molecule. Therefore, increasing the chain length or ascending homologous series increases the aggregation number of spherical micelles. For surfactants whose hydrocarbon portion is a single normal alkyl chain, the maximum aggregation numbers consistent with spherical shape are approximately 27, 39, 54, 72, and 92 for $C_8$, $C_{10}$, $C_{12}$, $C_{14}$ and $C_{16}$, respectively. If the surfactant concentration is increased beyond a few percent and if electrolytes are added (in the case of ionic surfactants) or the temperature is raised (in the case of nonionic surfactants), the micelles increase in size. Under these conditions, the micelles are too large to remain spherical and become ellipsoidal, cylindrical or finally lamellar in shape.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127® (Wyandotte Chemicals Corp.). Preferred surfactants are nonionic polyoxyethylene and polyoxypropylene detergents compatible with IV injection such as PLURONIC F-127®, n-octyl-β-D-glucopyranoside, and the like. In addition, phospholipids, such as those described for use in the production of liposomes, may also be used for micelle formation.

Since the MHC subunits of the present invention comprise a lipophilic transmembrane region and a relatively hydrophilic extracellular domain, mixed micelles are formed in the presence of common surfactants or phospholipids and the subunits. The mixed micelles of the present invention may comprise any combination of the subunits, phospholipids and/or surfactants. Thus, the micelles may comprise subunits and detergent, subunits in combination with both phospholipids and detergent, or subunits and phospholipid.

For pharmaceutical compositions which comprise the complexes of the present invention, the dose will vary according to, e.g., the particular complex, the manner of administration, the particular disease being treated and its severity, the overall health and condition of the patient, and the judgment of the prescribing physician. Dosage levels for murine subjects are generally between about 10 μg and about 500 μg. A total dose of between about 50 μg and about 300 μg, is preferred. For instance, in treatments provided over the course of a disease, three 25 μg or 100 μg doses are effective. Total dosages range between about 0.5 and about 25 mg/kg, preferably about 3 to about 15 mg/kg.

The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered intravenously. Thus, this invention provides compositions for intravenous administration which comprise a solution of the complex dissolved or suspended in an acceptable carrier, preferably an aqueous carrier. A variety of aqueous carriers may be used, e.g., water, buffered water, 0.4% saline, and the like. For instance, phosphate buffered saline (PBS) is particularly suitable for administration of soluble complexes of the present invention. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected. Preferred concentrations for intravenous administration are about 0.02% to about 0.1% or more in PBS.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the complexes can be administered for therapeutic, prophylactic, or diagnostic applications. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient. As discussed above, this will typically be between about 0.5 mg/kg and about 25 mg/kg, preferably about 3 to about 15 mg/kg.

In prophylactic applications, compositions containing the complexes of the invention are administered to a patient susceptible to or otherwise at risk of a particular disease. Such an amount is defined to be a "prophylactically effective dose." In this use, the precise amounts again depend on the patient's state of health and weight. The doses will generally be in the ranges set forth above.

In diagnostic applications, compositions containing the appropriately complexes or a cocktail thereof are administered to a patient suspected of having an autoimmune disease state to determine the presence of autoreactive T cells associated with the disease. Alternatively, the efficacy of a particular treatment can be monitored. An amount sufficient to accomplish this is defined to be a "diagnostically effective dose." In this use, the precise amounts will depend upon the patient's state of health and the like, but generally range from 0.01 to 1000 mg per dose, especially about 10 to about 100 mg per patient.

Kits can also be supplied for therapeutic or diagnostic uses. Thus, the subject composition of the present invention may be provided, usually in a lyophilized form in a container. The complexes, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of complex and usually present in total amount of at least about 0.001% wt. based again on the protein concentration. Frequently, it will be desirable to include an inert extender or excipient to dilute the active ingredients, where the excipient may be present in from about 1 to 99% wt. of the total composition. Where an antibody capable of binding to the complex is employed in an assay, this will usually be present in a separate vial. The antibody is typically conjugated to a label and formulated according to techniques well known in the art.

The following example illustrates, but does not limit, the invention.

EXAMPLES

Example 1

This example shows the binding of an N-terminal peptide of myelin basic protein MBP(1–14)$A^4$ to purified individual α and β chains of murine $IA^k$ molecules.

PROCEDURES

Purification of Murine $IA^k$ and $IA^s$ $IA^k$ and $IA^s$ was purified from NP-40 extracts of membrane prepared from cultured CH27 cells and SJL/J mouse spleen cells respectively, using an affinity support prepared by coupling monoclonal antibody, 10-2.16 (specific for $IA^k$ and $IA^s$), with Sepharose 4B beads by the standard cyanogen bromide coupling method as described in U.S. Pat. No. 5,130,297, which is incorporated herein by reference. Affinity-purified $IA^k$ and $IA^s$ molecules were characterized by 12% one-dimensional SDS polyacrylamide gel electrophoresis.

Isolation of α and β Subunits of MHC Molecules

Purified $IA^k$ was concentrated to 1 mg/ml using Amicon concentrators and applied onto a 12% preparative (16 cm×18 cm) slab gel unit. The electrophoresis was conducted under non-reducing conditions for 16 hours at room temperature at constant volts (100 volts). One lane was excised from the center of the gel and developed by silver staining. Using the stained gel lane as a guide, bands of α and β chains were excised and the proteins were electroeluted at 400 mA for 4 hours in an Amicon Electroeluter unit in the presence of 0.1% SDS. Eluted chains were concentrated, dialyzed against PBS containing 1% OG and characterized on native and reduced SDS polyacrylamide gels.

Synthesis of Peptides

The rat myelin basic protein peptide analog of MBP (1–14)$A^4$, with the sequence, Ac-ASQARPSQRHGSKY (SEQ ID NO:3), MBp(89–101)$Y^{89}$ peptide representing the sequence YFKNIVTPRTPPP (SEQ ID NO:4) and the ovalbumin peptide, OVA(323–340)$Y^{340}$, with the sequence, ISQAVHAAHAEINEAGRY (SEQ ID NO:5) were synthesized by the standard solid phase methodology using side-chain protected Fmoc amino acids and an Applied Biosystems 431A automated peptide synthesizer. Deprotected, crude peptide amides were purified by reverse-phase HPLC, and the homogeneity and identity of the purified peptides were confirmed by mass spectroscopic analysis.

Peptide Binding Assay

Peptide binding to α/β heterodimers or isolated chains of $IA^k$ was analyzed by thin layer chromatography (TLC) and by cellulose acetate electrophoresis (CAE) as described earlier. Briefly, synthetic MBP(1–14)$A^4$ and OVA(323–340)$Y^{340}$ peptides were radiolabeled with [$^{125}$I] using the Chloramine-T method at neutral pH. Intact $IA^k$ at a concentration of 200 µg/ml or each chain at a concentration of 100 µg/ml was incubated in a total volume of 100 µl with a 50 fold molar excess of radiolabeled peptide at 37° C. for 48 hours. The excess unbound peptide was removed by extensive dialysis against PBS containing 0.1% OG detergent at 4° C. for 36 hours. One µl of complex was applied in triplicate onto a 5 cm silica gel TLC plate and run in a solvent system of 50% methanol and 5% ammonium acetate. The plate was dried, and the distribution of radioactivity was estimated at $R_f$0–0.2 for calculating the percent of $IA^k$ or chains occupied with labeled peptide.

Peptide binding was also measured by CAE in which 1 µl of complex was applied at the center of cellulose polyacetate paper strips (2.5 cm×15.2 cm), and electrophoresis was performed at 350 constant volts for 10 min in the presence of high resolution Tris/Barbital (32.1% w/w Tris, 13.7% w/w Barbital and 54.2% w/w Sodium barbital) buffer pH at 8.1. Strips were dried, and the origin was counted for calculating the percent of $IA^k$ or chain occupied with labeled peptide.

Preparation of Chain:Peptide Complexes

Two types of complexes were prepared and purified. For peptide binding and T cell binding assays, complexes of unlabeled heterodimer or individual chain with radiolabeled peptides were prepared as described above. For T cell extracellular acidification rate measurements, unlabeled class II or chains and unlabeled peptide were used under identical conditions, and the complexes were dialyzed against bicarbonate-free, low-buffering RPMI 1640 medium, pH 7.4, containing 1 mM sodium phosphate, penicillin and streptomycin.

T Cell Binding Assay

Purified complexes of radiolabeled peptide and non-radiolabeled Ia dimer or monomers were incubated with 2.6× 10$^5$ resting T cells in 15 ml polypropylene tubes precoated with 1 mg/ml BSA solution at 37° C. in a $CO_2$ incubator. For the antibody blocking experiment, cells were first incubated with 500 µg of affinity purified hamster anti-mouse α/β TCR monoclonal antibody (Pharmingen, San Diego, Calif.) before the addition of labeled complexes. Purified hamster IgG isotype standard antibody, specific for TNP (Pharmingen, San Diego, Calif.) was used as a negative control antibody. At the end of the incubation period, 15 ml of chilled PBS was added to each tube. The cells were resuspended gently, centrifuged at 2,000×g, and the supernatant was carefully removed. The washing procedure was repeated three times, and the cell pellet was counted in a gamma counter.

Measurement of T Cell Metabolic Acidification Rate

The details of the loading of T cells into the microphysiometer for the acidification rate measurements are described in Owicki et al., above. Briefly, cells were rested from antigen pulsing for 10 days and cultured overnight in low serum (2.5%) medium to lower their basal metabolic activity. The cells were harvested and resuspended in serum-free loading medium (low buffering RPMI 1640 containing 10 mM HEPES buffer, pH 7.3) at 1×10$^7$ cells/ml. Extracellular acidification measurements were made in the microphysiometer collecting potentiometric measurements for 1 min. every 2.5 min. Acidification rate data (Volts/sec) were mathematically normalized to 100% prior to cell stimulation which allows the comparison of data from cells in separate chambers.

RESULTS

Alpha and beta chains of affinity-purified $IA^k$ were electroeluted from a non-reducing polyacrylamide gel and characterized by SDS polyacrylamide gel electrophoresis as shown in FIG. 5. Dissociation of α/β heterodimer into α and β chains can be achieved either by incubating purified $IA^k$ at 95° C. for 5 min (as shown in Panel A) or by exposing pH 3.0 for 1 hour at 4° C. (Panel B). Both conditions resulted in significant dissociation of the dimer into monomers. Since incubation at high temperature is more likely to denature the MHC class II chains, low pH treatment was used as a method for monomer enrichment. Individual chains purified by the electroelution method are free of any cross contamination. Occasionally, the chain preparations from different batches contained 5-15% homodimers. As expected, the homodimer bands migrate at a mobility close to the α/β heterodimer position. To make sure that the high molecular weight band at around 60 kD in the native gel is not due to any cross contamination of chains, the chain preparations were analyzed by SDS-PAGE after reduction with 2-ME as shown in Panel C. Silver staining of the gel did not show any detectable cross contaminant α or β band. The relative amount of homodimers present in the chain preparation was quantitated by scanning the native gel lanes for both α and β chains. As shown in Panels D and E, the α and the β polypeptide preparations used in this study contain 8.6% and 12.9% homodimers, respectively.

Binding of peptide to purified α and β chains was carried out at pH 8.0 which has been reported to be optimal for the binding of MBP(1–14)$A^4$ peptide to $IA^k$. In both peptide binding assays, as shown in FIGS. 6A and 6B, 30–34% of both α and β chains was occupied with this peptide. The α/β heterodimer isolated under identical conditions, showed 25% occupancy with the MBP(1–14)$A^4$ peptide. Specificity of the binding of the MBP(1–14)$A^4$ peptide to the individual chains of $IA^k$ was shown by incubating [$^{125}$I]-labeled ovalbumin peptide OVA(323–340)$Y^{340}$ with α and β chains of $IA^k$ each of which showed only 2-3% binding of peptide.

Figure 7A:
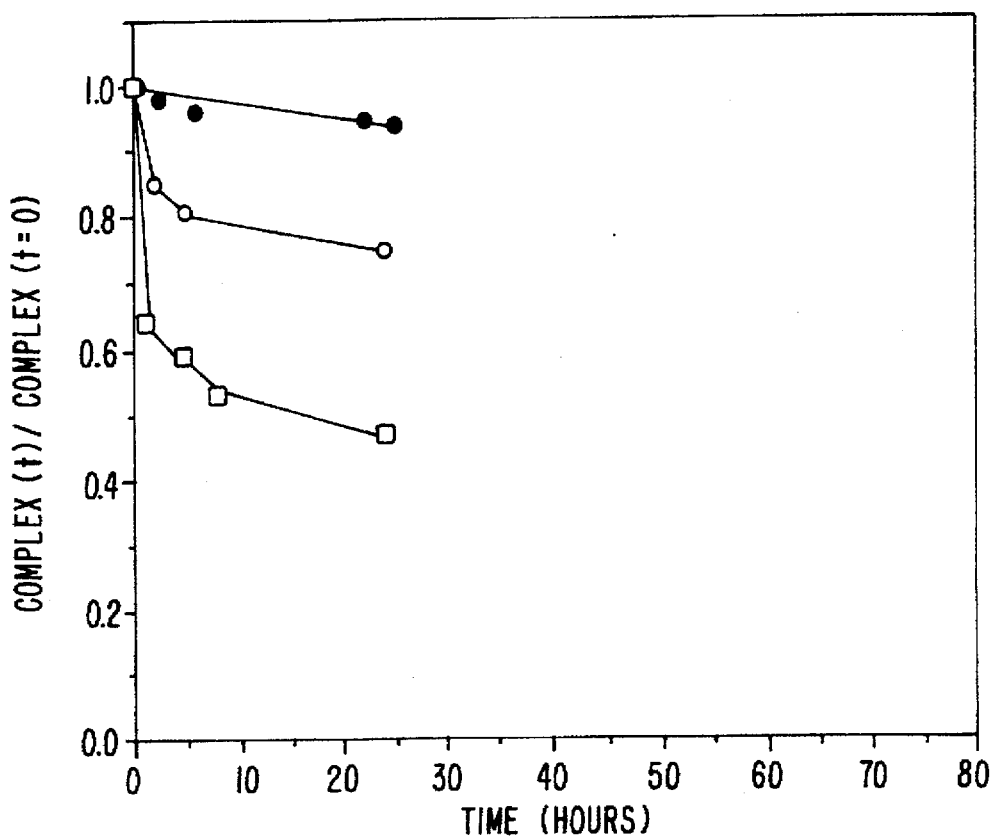
FIGS. 7A and 7B show the stability of single-chain:peptide complexes of the invention.
Figure 7B:
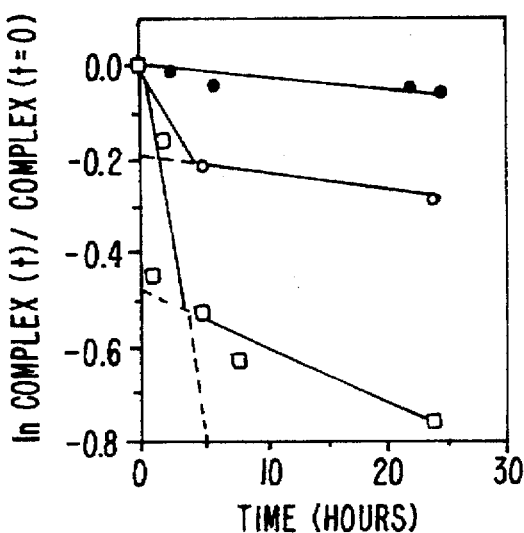

The stability of single chain:peptide complexes at 37° C. in PBS containing 1% OG is presented in FIG. 7. Incubation of β chain:MBP(1–14)$A^4$ complexes at 37° C. for 1 hour led to 40% dissociation. In contrast, only 20% dissociation of α chain:MBP(1–14)$A^4$ complexes and 5% dissociation of $IA^k$:MBP(1–14)$A^4$ complexes were observed over a period of 24 hours at 37° C. The dissociation observed for the α:MBP(1–14)$A^4$ and β:MBP(1–14)$A^4$ are clearly biphasic. For the initial phase, β:MBP(1–14)$A^4$ complexes have a higher dissociation rate ($k_d$=6.2×10$^{-6}$ sec$^{-1}$). However, for the second phase of the dissociation, the slopes of the α/β:MBP(1–14)$A^4$ and α:MBP(1–14)$A^4$ complexes are almost identical with $k_d$ values of 5×10$^{-7}$ sec$^{-1}$ and 7×10$^{-7}$ sec$^{-1}$ respectively. The slope of the second phase of β:MBP(1–14)$A^4$ complexes had a $k_d$ value of 6.2×10$^{-6}$ sec$^{-1}$.

Example 2

This example shows that single chain complexes of isolated α and β chains with antigenic peptide can bind to and stimulate T cells.

Using complexes of radiolabeled peptide and unlabeled chains, direct binding of chain:peptide complexes to cloned T cells was measured, and the number of complex molecules associated with cells was calculated. T cell clone 4R3.9, which recognizes MBP(1–14) in the context of $IA^k$, was incubated with purified single chain complexes containing [$^{125}$I]:MBP(1–14)A4 peptide. Since T cells are very sensitive to detergent, for cell binding and stimulation assays complexes that were dialyzed against detergent-free low buffering RPMI 1640 medium or PBS buffer were used. The results presented in FIG. 8A demonstrate that the binding of α chain:MBP(1–14)$A^4$ complexes to 4R3.9 cloned T cells is comparable to that of intact $IA^k$:MBP(1–14)$A^4$ complexes. However, the β chain:MBP(1–14)$A^4$ complexes showed lower binding affinity to 4R3.9 T cells. The association of MHC class II peptide complexes to T cells was complete by 6 hours at 37° C., the number of complex molecules associated per T cell was calculated and found to be 2.55× 10$^6$, 2.1×10$^6$ and 1.0×10$^6$ for $IA^k$:MBP(1–14)$A^4$, α chain:MBP(1–14)$A^4$ and β chain:MBP(1–14)$A^4$ complexes, respectively. The number of complex molecules bound per T cell were higher than the reported number of TCRs on the T cell surface, 2.5–5.0×10$^4$ to 1×10$^5$ which could be due to the aggregation level of the complexes in the absence of detergent. The specificity of the chain-peptide complex binding to the T cells was confirmed by incubating complexes of α and β chains of $IA^k$ and [$^{125}$I]:MBP(1–14)A4 peptide with the HS-1 T cell clone, restricted for $IA^s$ and MBP(90–103) complexes.

Figure 8C:
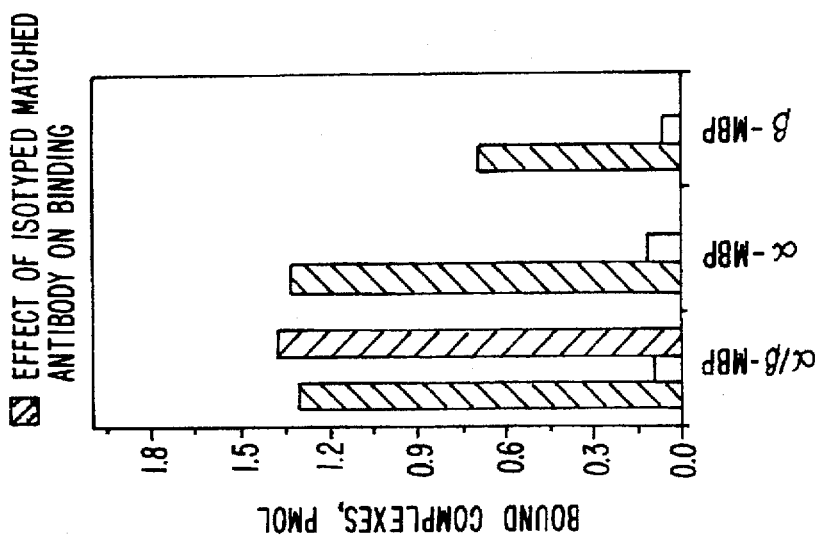
FIG. 8C shows the ability of complexes of the invention to bind TCR, as demonstrated by a blocking experiment using anti-TCR monoclonal antibodies.
Figure 8B:
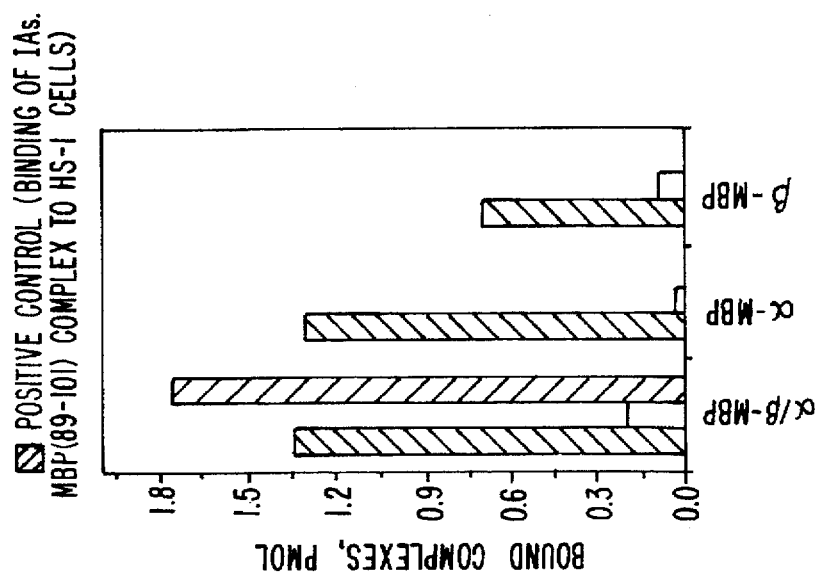
FIG. 8B. shows preferenetial binding of both heterodimer complexes and single-chain complexes to T cells.
Figure 8A:
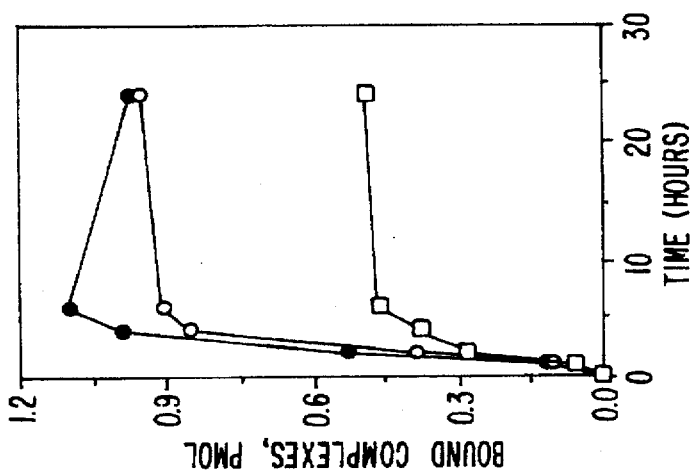
FIG. 8A. demonstrates the binding of $\alpha$ chain complexes to cloned T cells.

As shown in FIG. 8B, preferential binding of all three complexes to 4R3.9 T cells, restricted for $IA^k$ and MBP (1–14) peptide was observed as compared to the HS-1 T cells. In a positive control experiment, incubation of $IA^s$:MBP(89–101)$Y^{89}$ complexes showed the expected strong binding to HS-1 cloned T cells. The binding of chain-peptide complexes to TCRs of 4R3.9 T cells was also confirmed by an antibody blocking experiment where cells pretreated with α/β anti-TCR monoclonal antibody failed to bind complexes (FIG. 8C). Cells preincubated with isotyped matched antibody under identical conditions showed no inhibition of binding.

In order to determine whether isolated chain:peptide complexes trigger an in vitro T cell response, we used a microphysiometer that measures extracellular acidification rate of ligand-mediated cell triggering.

Measurement of T Cell Metabolic Acidification Rate:

The details of the loading of T cells into the microphysiometer for the acidification rate measurements are described in Owicki et el., above. Briefly, cells were rested from antigen pulsing for 10 days and cultured overnight in low serum (2.5%) medium to lower their basal metabolic activity. The cells were harvested and resuspended in serum-free loading medium (low buffering RPMI 1640 containing 10 mM HEPES buffer, pH 7.3) at 1×10$^7$ cells/ml. Extracellular acidification measurements were made in the microphysiometer collecting potentiometric measurements for 1 min. every 2.5 min. Acidification rate data (Volts/sec) were mathematically normalized to 100% prior to cell stimulation which allows the comparison of data from cells in separate chambers.

Figure 9A:
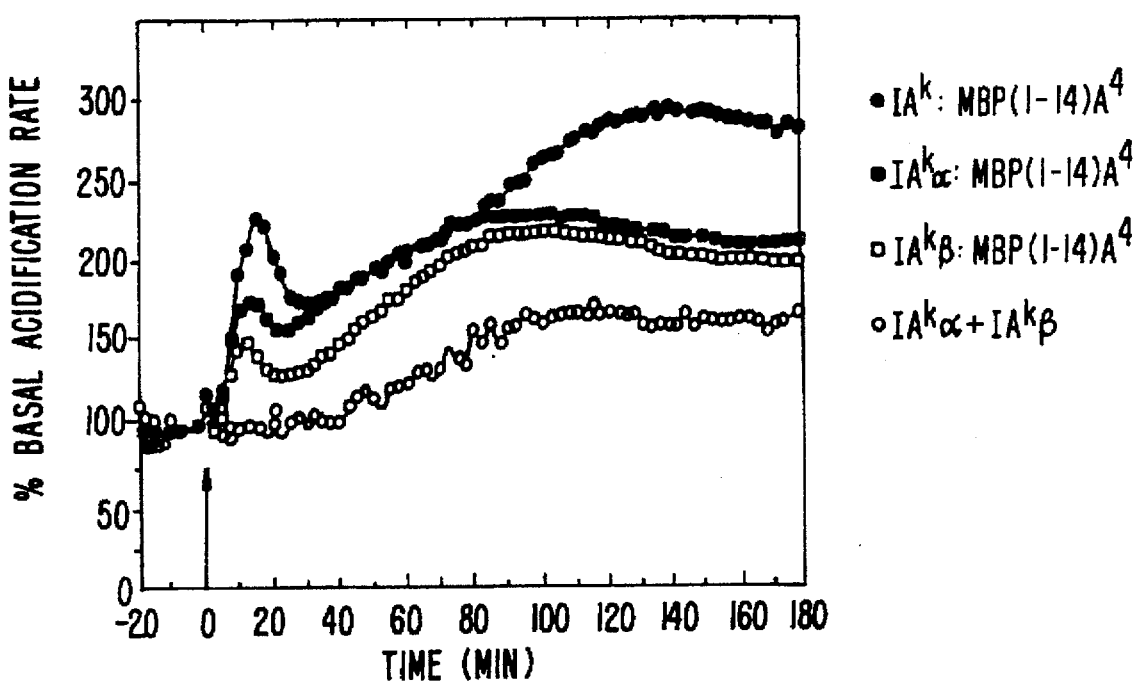
FIG. 9A shows the sustained increase in acidification of the medium induced by interaction between complexes of the invention and T cells, as measured by the microphysiometer.
Figure 9B:
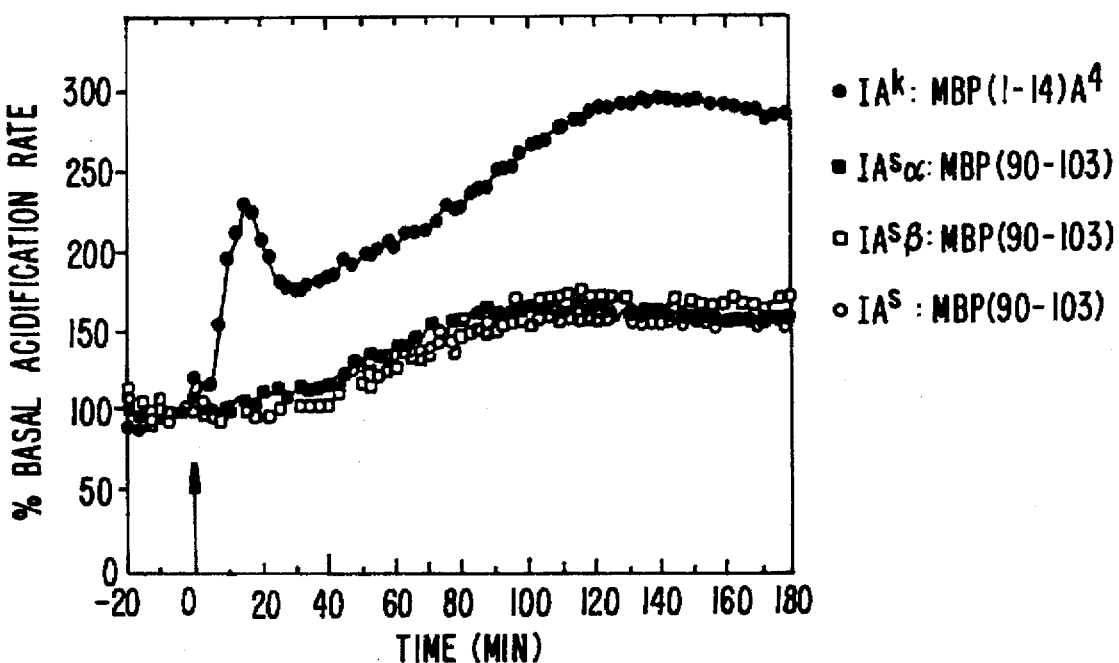
FIG. 9B shows that non-specific complexes do not induce significant increase in acidification.

A specific T cell response within minutes of the interaction of complexes with TCR was observed when the resting 4R3.9 T cells were exposed to single chain:peptide complexes. A rapid, sustained increase in the acidification rate, characteristic of intact $IA^k$:MBP(1–14)$A^4$ complexes and T cell interaction, was observed when 4R3.9 T cells were exposed to α chain-MBP(1–14)$A^4$ complexes as shown in FIG. 13A. The complexes of β chain:MBP(1–14)$A^4$ peptide also induced the increased acidification rate in 4R3.9 cells, but not to the same extent as the α-chain complex, which was slightly more potent. The intact $IA^k$:MBP(1–14)$A^4$ complex gave the highest level of T cell stimulation, which became more apparent after about 2 hr post complex treatment. The specificity of the $IA^k$ chain:peptide complex activation of T cells was demonstrated by the lack of increased acidification rates when an equimolar mixture of α and β was used to treat T cells as shown in FIGS. 9A and 9B. In several experiments, α and β chains without peptide gave no increase in acidification rate over medium alone. In the same set of experiments (FIG. 9B), several non-specific MHC complexes, $IA^s$:MBP(89–101)$Y^{89}$, $IA^s$ α chain:MBP (89–101)$Y^{89}$, and $IA^s$ β chain:MBP(89–101)$Y^{89}$ did not induce significant increases in the acidification rate.

CONCLUSIONS

In summary, the results presented here demonstrate that the isolated chains of MHC class II molecules can bind antigenic peptide and that complexes of isolated chains of MHC class II molecules and antigenic peptide are recognized by MHC class II restricted TCRs on T cells. In the case of the T cell clone, 4R3.9, this binding leads to a specific T cell stimulation similar to that induced by intact heterodimer. The present work indicates that intact α/β heterodimers on the cell surface is not always required for antigen presentation.

Example 3

This example demonstrates that complexes of the invention induce a state of proliferative nonresponsiveness, or clonal anergy, in cloned T cell lines. To do this, individually isolated α and β chains, dimeric and monomeric forms of $IA^s$ were complexed with MBP 90–101 and incubated in the presence of HS-1 cloned T cells. $IA^s$:MBP 90–101 complexes are specifically recognized by the murine T cell clone HS-1. Irrelevant complexes used as controls were the latter of these two complexes not specifically recognized by one particular clone.

Cloned T cell lines. HS-1 T cell clones are restricted by MBP 90–101 presented by $IA^s$ expressing antigen presenting cells. 4R3.9 T cell clones are restricted by MBP rl-14 presented by $IA^k$ expressing antigen presenting cells. Both clones are subjected to antigen pulsing on ten day cycles.

Induction of in vitro T cell nonresponsiveness. Residual antigen presenting cells were removed by subjecting T cell clones (10 days following antigen pulsing) to two rounds of 19% metrizamide density gradient centrifugation, followed by two washes in RPMI 1640 medium. T cell clones ($1\times10^6$) were cultured each in the presence of appropriate, nonappropriate control complexes, and a ten-fold molar excess of the corresponding peptide used in preparation of the complexes for 24 hours at 37° C. Additional controlled conditions were introduced as required. HS-1 cells were washed four times and $8\times10^4$ T cells were cultured in triplicate with $5\times10^5$ freshly irradiated SJL/J spleen cells in the presence of 0, 5, 10, or 20 μM MBP 90–101 peptide or with only 20 U/ml IL-2. During the final eight hours of a 72 hour incubation at 37° C., 1 μCi of $^3$H-thymidine was added and the degree of proliferation was measured by incorporated radioactivity.

RESULTS AND CONCLUSIONS

Figure 10A:
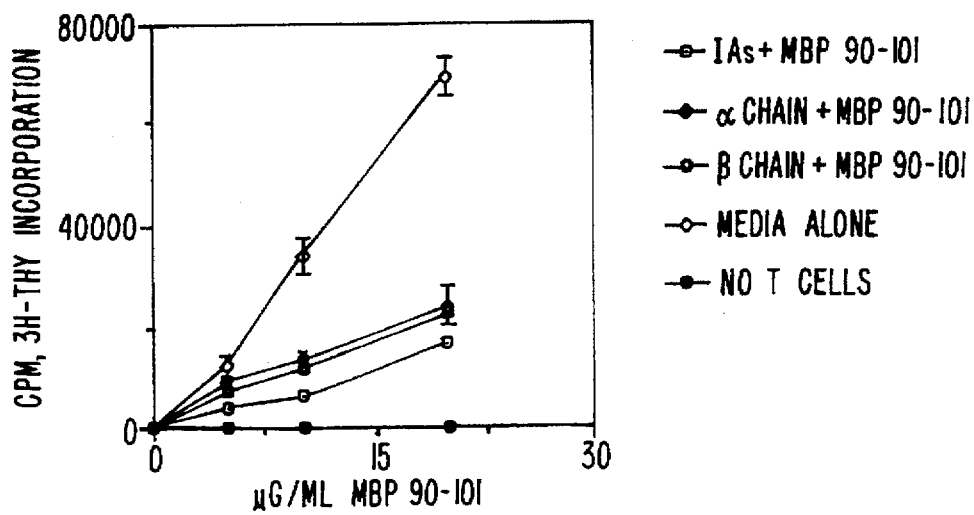
FIGS. 10A, B and C show significant induction of anergy in T cells by complexes of the invention.
Figure 10B:
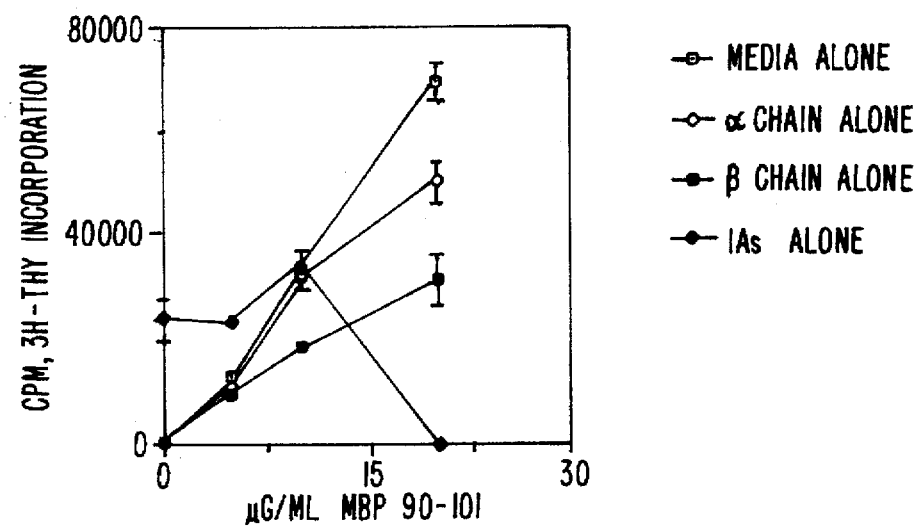
Figure 10C:
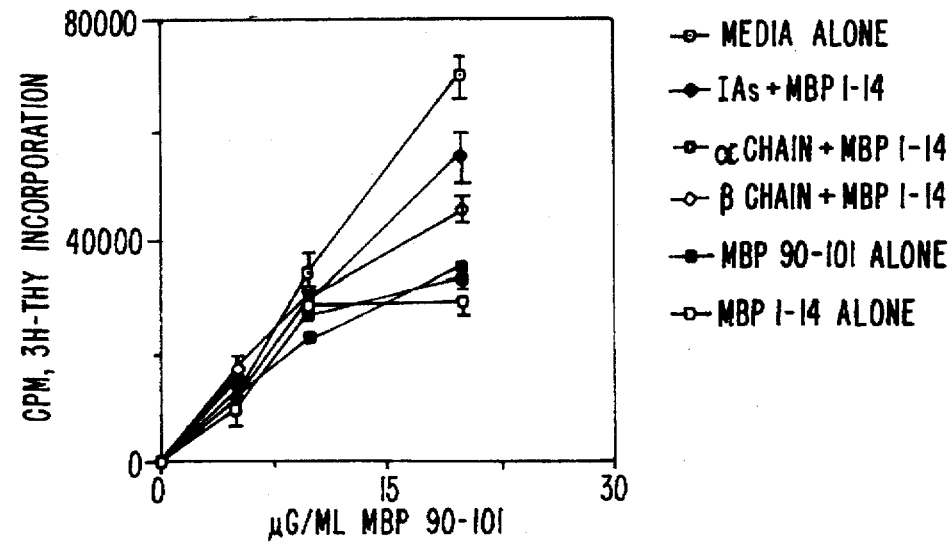

FIG. 10 illustrates a significant anergic response of HS-1 cells to each relevant complex composed of either dimer, α chain, or β chain $IA^s$ components. The antigenic proliferative responsiveness was reduced by at least a factor of two throughout the range of control responses observed. The anergic responses to α chain complexes and β chain complexes were relatively similar and were not significantly different from the dimer complexes.

Figure 11A:
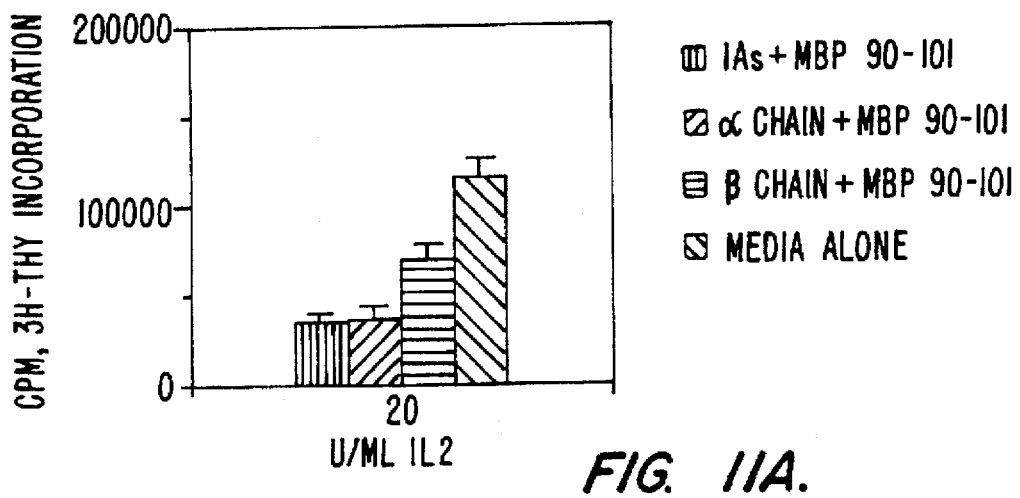
FIGS. 11A, B and C show induction of anergy as measured by IL-2 production.
Figure 11B:
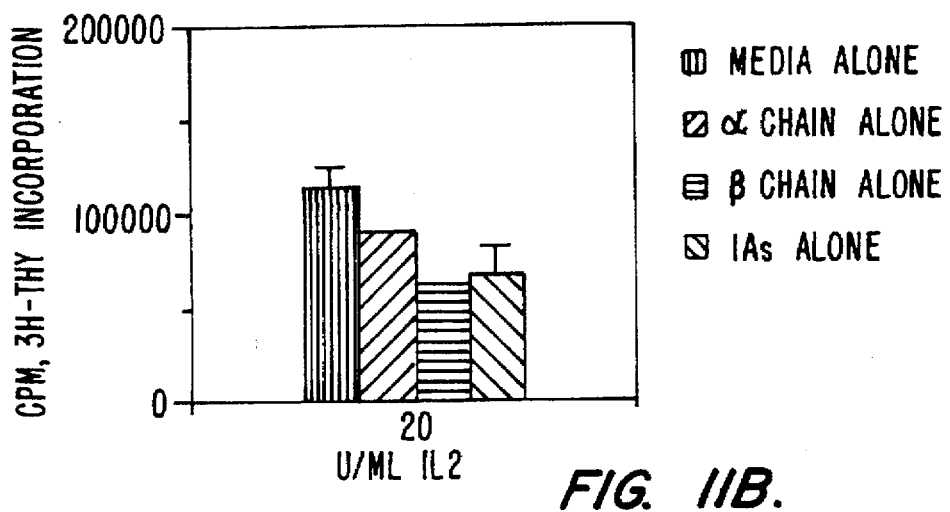
Figure 11C:
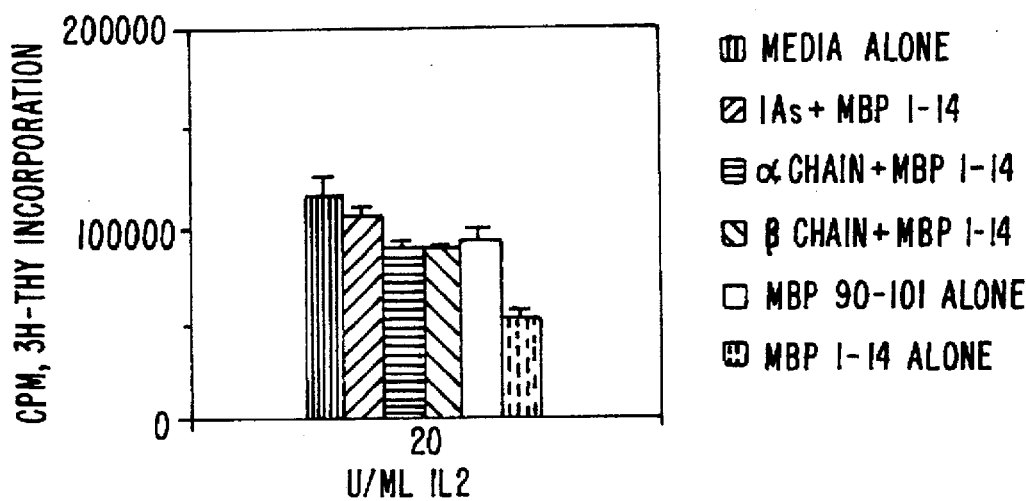

FIG. 11 portrays the IL-2 responsiveness of these same cells following complex treatment. Anergic cells have been reported to be sensitive to IL-2 although their proliferative response is significantly reduced compared to cells not rendered anergic. HS-1 cells exposed to the dimeric form of $IA^s$ complexes and $IA^s$ α chain complexes exhibit a decreased response while complexes made up of only β chain exhibit an IL-2 response equivalent to that of the controls.

Example 4

This example demonstrates the ability of the single chain complexes of the invention to induce anergy in vivo. These experiments demonstrate prevention of EAE in SJL/J mice. The experiments were performed generally as described in Sharma et al., Proc. Natl. Acad. Sci. USA 88:11465–11469 (1991), which is incorporated herein by reference. Briefly, α and β chains of $IA^s$ were purified from affinity purified $IA^s$ by the preparative electroelution method described above.

Figure 12:
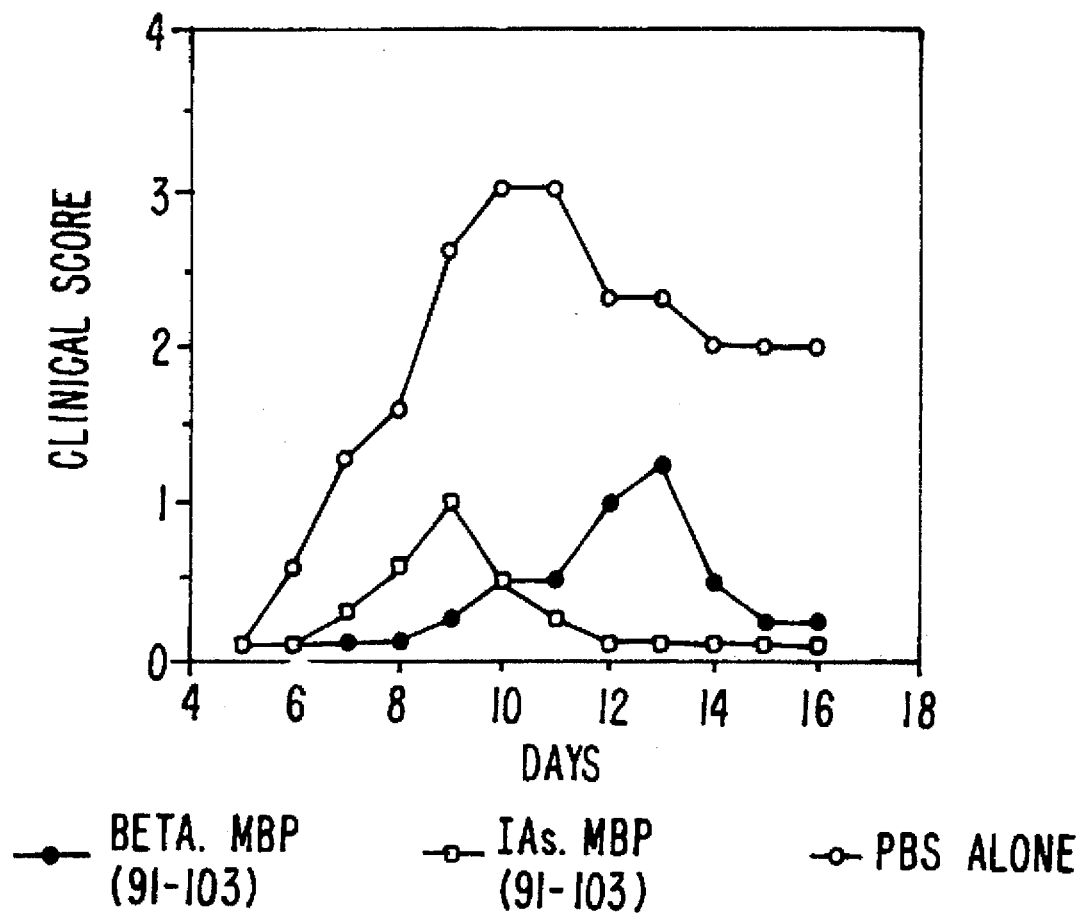
FIG. 12 shows attenuation of EAE in mice treated with complexes of the invention.

EAE was induced by adoptive transfer of $1.2\times10^7$ MBP (91–103) reactive T cells as described in Sharma et al. The experiment was performed using β chain of $IA^s$ complexed with MBP 91–103 peptide prepared as described above. On days 0, 3, and 7, each mouse received 7.5 μg of complexes in 0.5 ml as described in Sharma et al. The results are shown in FIG. 12 and Table I.

TABLE 1

Prevention of acute EAE with injection of β chain of
I—As molecule coupled to MBP p91-103

| | No paralysed | Day onset | Mean severity |
|---|---|---|---|
| β: MBP91-103 | 0/4 | — | — |
| β: MBP1-14 | 2/4 | 15 | 1.5 |
| α: MBP91-103 | 3/4 | 24 | 1.25 |
| β alone | 2/4 | 18 | 1.5 |
| saline | 3/4 | 12 | 1.5 |

Example 5

The results presented below demonstrate that MHC-peptide complexes comprising dimeric MHC molecules exist primarily as aggregates in the absence of detergent.

Figure 13:
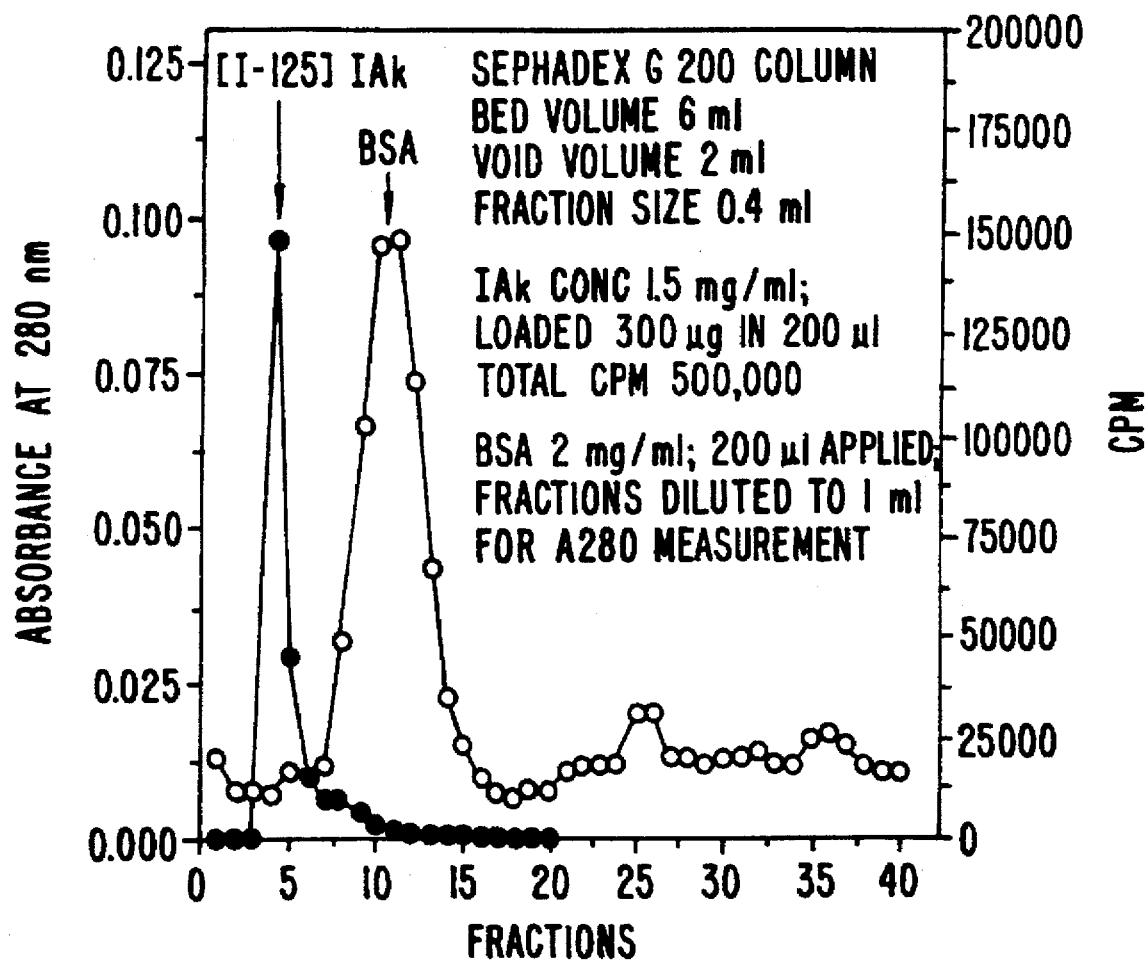
FIG. 13 shows that dimeric MHC-peptide complexes exist as aggregates because they pass through the column with the void volume and thus have a molecular weight greater than 600,000.

An $IA^k$-P complex labeled with $^{125}$I was prepared as described in U.S. Pat. No. 5,130,297, above. The complex (1.5 mg/ml) was dialysed extensively against phosphate buffered saline (PBS) to remove detergent and loaded on a 6 ml b.v. Sephadex-G200 column (fractionation size 5000–600,000). The results presented in FIG. 13 show that the aggregated complexes pass through the column with the void volume and thus have a molecular weight greater than 600,000.

The same dialyzed $IA^k$ complex (1.5 mg/ml) was also, centrifuged and the pellet was counted. To do this, 200 μl of complex (300 μg) was diluted in 5 ml PBS and centrifuged in a fixed angle rotor at 100,000×g for 60 minutes. The results are given in Table 2, below.

TABLE 2

DETECTION OF COMPLEX AGGREGATION BY HIGH SPEED SPIN

| EXP # | Starting cpm | cpm in pellet | cpm in sup | % aggreg. |
|---|---|---|---|---|
| 1 | 514,576 | 317,717 | 205,797 | 60.68 |
| 2 | 519,340 | 321,304 | 209,108 | 60.57 |

The results of the chromatography and centrifugation experiments both show that MHC-peptide complexes exist largely in aggregated or micellar form. These results strongly indicate that the single subunit complexes of the present invention are also aggregated or in micellar form, in the absence of detergent.

Although the invention has been described in some detail in these examples for purposes of clarity and understanding, it will be apparent that certain changes and modifications may be practiced within the scope of the appended claims.

---

What is claimed is:

1. A method for preparing an MHC single-chain-peptide complex comprising an autoantigenic peptide and an MHC Class II β chain component having an antigen binding site, the complex capable of binding a T cell, the method comprising:

contacting an isolated MHC Class II β chain component with an autoantigenic peptide such that the autoantigenic peptide is coupled to the antigen binding site to form a complex.

2. The method of claim 1 further comprising the step of removing excess autoantigenic peptide by dialysis.

3. The method of claim 1 further comprising the step of dialyzing the complex in the presence of lipids to form liposomes.

4. The method of claim 1 wherein the autoantigenic peptide is noncovalently bound to the antigen binding site.

5. The method of claim 1 wherein the autoantigenic peptide has no more than 20 amino acids.

6. The method of claim 1 wherein the autoantigenic peptide comprises amino acids 1–14 of MBP.

7. The method of claim 1 further comprising the step of attaching an effector component to the complex.

* * * * *